US006908636B2

(12) United States Patent
Howarth

(10) Patent No.: US 6,908,636 B2
(45) Date of Patent: Jun. 21, 2005

(54) MICROBIOLOGICAL CONTROL IN POULTRY PROCESSING

(75) Inventor: Jonathan N. Howarth, Baton Rouge, LA (US)

(73) Assignee: Albermarle Corporation, Richmond, VA (US)

( * ) Notice: Subject to any disclaimer, the term of this patent is extended or adjusted under 35 U.S.C. 154(b) by 288 days.

(21) Appl. No.: 10/029,329

(22) Filed: Dec. 21, 2001

(65) Prior Publication Data

US 2005/0100643 A1 May 12, 2005

Related U.S. Application Data

(63) Continuation-in-part of application No. 09/893,581, filed on Jun. 28, 2001, now abandoned.

(51) Int. Cl.$^7$ .............................. A23C 21/00; A23B 4/14
(52) U.S. Cl. ...................... 426/310; 320/331; 320/335; 320/532
(58) Field of Search .................... 452/173; 426/310, 426/320, 331, 332, 335, 532, 644

(56) References Cited

U.S. PATENT DOCUMENTS

| | | | |
|---|---|---|---|
| 2,130,805 A | 9/1938 | Levine | |
| 2,392,505 A | 1/1946 | Rogers | |
| 2,398,598 A | 4/1946 | Rogers | |
| 2,779,764 A | 1/1957 | Paterson | |
| 2,795,556 A | 6/1957 | Quinn | |
| 2,868,787 A | 1/1959 | Paterson | |
| 2,920,997 A | 1/1960 | Wolf et al. | |
| 2,971,959 A | 2/1961 | Waugh et al. | |
| 2,971,960 A | 2/1961 | Waugh et al. | |
| 3,121,715 A | 2/1964 | Waugh et al. | |
| 3,147,219 A | 9/1964 | Paterson | |
| 3,147,259 A | 9/1964 | Paterson | |
| 3,152,073 A | 10/1964 | Morton ......................... | 210/62 |
| 3,170,883 A | 2/1965 | Owen et al. ................. | 252/187 |
| 3,308,062 A | 3/1967 | Gunther ....................... | 210/58 |
| 3,328,294 A | 6/1967 | Self et al. ..................... | 210/62 |
| 3,345,371 A | 10/1967 | Paterson | |
| 3,412,021 A | 11/1968 | Paterson | |
| 3,558,503 A | 1/1971 | Goodenough et al. ...... | 252/187 |
| 3,589,859 A | 6/1971 | Foroulis ....................... | 21/2.7 |
| 3,626,972 A | 12/1971 | Lorenzen | |
| 3,711,246 A | 1/1973 | Foroulis ....................... | 21/2.7 |
| 3,749,672 A | 7/1973 | Golton et al. ................ | 252/95 |
| 3,767,586 A | 10/1973 | Rutkiewic .............. | 252/187 H |
| 4,032,460 A | 6/1977 | Zilch et al. ............. | 252/8.55 B |
| 4,078,099 A | 3/1978 | Mazzola | |
| 4,119,535 A | 10/1978 | White et al. | |
| 4,126,717 A | 11/1978 | Mazzola | |
| 4,136,052 A | 1/1979 | Mazzola | |
| 4,199,001 A | 4/1980 | Kratz | |
| 4,237,090 A | 12/1980 | DeMonbrun et al. ......... | 422/13 |
| 4,242,216 A | 12/1980 | Daugherty et al. | |
| 4,270,565 A | 6/1981 | King, Sr. | |
| 4,293,425 A | 10/1981 | Price | |
| 4,295,932 A | 10/1981 | Pocius ......................... | 162/161 |
| 4,327,151 A | 4/1982 | Mazzola | |
| 4,331,174 A | 5/1982 | King, Sr. | |
| 4,382,799 A | 5/1983 | Davis et al. ................... | 8/107 |
| 4,388,811 A | 6/1983 | Zebarth | |
| 4,427,435 A | 1/1984 | Lorenz et al. ................. | 71/67 |
| 4,427,692 A | 1/1984 | Girard | |
| 4,451,376 A | 5/1984 | Sharp ......................... | 210/701 |
| 4,465,598 A | 8/1984 | Darlington et al. ......... | 210/721 |
| 4,465,839 A | 8/1984 | Schulte et al. | |
| 4,476,930 A | 10/1984 | Watanabe ................... | 166/279 |
| 4,490,308 A | 12/1984 | Fong et al. ............. | 260/513 N |
| 4,532,330 A | 7/1985 | Cole | |
| 4,534,963 A | 8/1985 | Gordon | |
| 4,537,697 A | 8/1985 | Girard | |
| 4,539,071 A | 9/1985 | Clifford et al. ............. | 162/161 |
| 4,546,156 A | 10/1985 | Fong et al. ................. | 526/240 |
| 4,560,766 A | 12/1985 | Girard et al. | |
| 4,566,973 A | 1/1986 | Masler, III et al. ......... | 210/701 |
| 4,571,333 A | 2/1986 | Hsiao et al. | |
| 4,595,517 A | 6/1986 | Abadi ......................... | 252/82 |

(Continued)

FOREIGN PATENT DOCUMENTS

| | | |
|---|---|---|
| CA | 1230825 | 12/1987 |
| CA | 2042430 | 11/1991 |
| CA | 2163598 | 9/1996 |
| EP | 0106563 | 4/1984 |
| EP | 0177645 | 4/1986 |
| EP | 0206725 | 12/1986 |
| EP | 0228593 | 7/1987 |
| EP | 0550137 | 7/1993 |
| EP | 0581826 | 2/1994 |
| EP | 0584955 | 3/1994 |
| EP | 0827695 A2 | 3/1998 |

(Continued)

OTHER PUBLICATIONS

CABA Copyright 2002 CABI Abstract of Bukh, K., "Use of Chlorine in Experiments on Controlling Swine Dysentery", Dansk Veterinaertidsskrift, (1988), vol 71, No. 24, pp. 1278–1286. AN: 89:73404 CABA.

Ault et al., "Infrared and Raman Spectra of the $M^+Cl_{3-}$ ion Pairs and Their Chlorine–bromine Counterparts isolated in Argon Matrices", Journal of Chemical Physics, 1976, vol.: 64, No. 12, ppg. 4853–4859.

Willard et al., "Elementary Quantitative Analysis", Third Edition, Chapter XIV, 1933, ppg. 261–271.

(Continued)

Primary Examiner—Carolyn Paden

(57) ABSTRACT

In the processing of poultry, equipment, instruments, apparatus and/or water used in such processing, and/or carcasses and/or parts of poultry resulting from the processing of poultry, are disinfected with aqueous solutions of certain halogen-based microbiocides, especially certain bromine-based microbiocides. Described are the particular microbiocides used and the substantial advantages of using such materials, in some cases as concentrated solutions and in other cases as dilute solutions.

22 Claims, 10 Drawing Sheets

U.S. PATENT DOCUMENTS

| | | | |
|---|---|---|---|
| 4,595,691 A | 6/1986 | LaMarre et al. ............. 514/367 |
| 4,597,941 A | 7/1986 | Bottom et al. |
| 4,604,431 A | 8/1986 | Fong et al. ................. 525/351 |
| 4,621,096 A | 11/1986 | Cole |
| 4,642,194 A | 2/1987 | Johnson ....................... 210/699 |
| 4,643,835 A | 2/1987 | Koeplin-Gall et al. ...... 210/754 |
| 4,654,424 A | 3/1987 | Girard et al. |
| 4,659,359 A | 4/1987 | Lorenz et al. ................. 71/67 |
| 4,661,503 A | 4/1987 | Martin et al. ............... 514/372 |
| 4,662,387 A | 5/1987 | King, Sr. |
| 4,677,130 A | 6/1987 | Puzig |
| 4,680,339 A | 7/1987 | Fong ........................ 525/54.11 |
| 4,680,399 A | 7/1987 | Buchardt .................... 546/139 |
| 4,681,948 A | 7/1987 | Worley ........................ 548/319 |
| 4,692,335 A | 9/1987 | Iwanski |
| 4,698,165 A | 10/1987 | Theyson |
| 4,703,092 A | 10/1987 | Fong ........................ 525/351 |
| 4,711,724 A | 12/1987 | Johnson ....................... 210/699 |
| 4,713,079 A | 12/1987 | Chun et al. |
| 4,728,453 A | 3/1988 | Choy |
| 4,745,189 A | 5/1988 | Lee et al. |
| 4,752,443 A | 6/1988 | Hoots et al. .................. 422/13 |
| 4,759,852 A | 7/1988 | Trulear ....................... 210/699 |
| 4,762,894 A | 8/1988 | Fong et al. ................. 525/344 |
| 4,767,542 A | 8/1988 | Worley ........................ 210/755 |
| 4,770,884 A * | 9/1988 | Hill et al. ................... 426/332 |
| 4,777,219 A | 10/1988 | Fong ........................ 525/329.4 |
| 4,780,197 A | 10/1988 | Schuman |
| 4,790,943 A | 12/1988 | Dunn et al. |
| 4,801,388 A | 1/1989 | Fong et al. .................. 210/701 |
| 4,802,990 A | 2/1989 | Inskeep, Jr. ................. 210/699 |
| 4,803,079 A | 2/1989 | Hsiao et al. |
| 4,822,512 A | 4/1989 | Auchincloss ................ 252/106 |
| 4,822,513 A | 4/1989 | Corby ........................ 252/106 |
| 4,846,979 A | 7/1989 | Hamilton .................... 210/754 |
| 4,860,554 A | 8/1989 | Innes et al. |
| 4,867,895 A | 9/1989 | Choy |
| 4,883,600 A | 11/1989 | MacDonald et al. ........ 210/696 |
| 4,886,915 A | 12/1989 | Favstritsky ................. 564/503 |
| 4,898,686 A | 2/1990 | Johnson et al. .......... 252/389.2 |
| 4,906,651 A | 3/1990 | Hsu ........................ 514/372 |
| 4,919,841 A | 4/1990 | Kamel et al. |
| 4,923,634 A | 5/1990 | Hoots et al. ............. 252/389.2 |
| 4,925,866 A | 5/1990 | Smith |
| 4,929,424 A | 5/1990 | Meier et al. ..................... 422/9 |
| 4,929,425 A | 5/1990 | Hoots et al. .................. 422/13 |
| 4,964,892 A | 10/1990 | Hsu |
| 4,966,716 A | 10/1990 | Favstritsky et al. ......... 210/755 |
| 4,992,209 A | 2/1991 | Smyk et al. ................. 252/387 |
| 4,995,987 A | 2/1991 | Whitekettle et al. ........ 210/754 |
| 5,034,155 A | 7/1991 | Soeder et al. ........... 252/389.23 |
| 5,035,806 A | 7/1991 | Fong et al. .................. 210/701 |
| 5,047,164 A | 9/1991 | Corby ........................ 252/106 |
| 5,055,285 A | 10/1991 | Duncan et al. ............. 423/473 |
| 5,057,612 A | 10/1991 | Worley et al. .............. 548/301 |
| 5,076,315 A | 12/1991 | King |
| 5,118,426 A | 6/1992 | Duncan et al. ............. 210/721 |
| 5,120,452 A | 6/1992 | Ness et al. .................. 210/754 |
| 5,120,797 A | 6/1992 | Fong et al. ............... 525/329.4 |
| 5,137,563 A | 8/1992 | Valkanas |
| 5,141,652 A | 8/1992 | Moore, Jr. et al. .......... 210/754 |
| 5,173,190 A | 12/1992 | Picek |
| 5,179,173 A | 1/1993 | Fong et al. ............... 525/329.4 |
| 5,192,459 A | 3/1993 | Tell et al. ................... 252/106 |
| 5,194,238 A | 3/1993 | Duncan et al. ............. 423/473 |
| 5,196,126 A | 3/1993 | O'Dowd .................... 210/754 |
| 5,202,047 A | 4/1993 | Corby ........................ 252/106 |
| 5,208,057 A * | 5/1993 | Greenley et al. ........... 426/332 |
| 5,218,983 A | 6/1993 | King |
| 5,259,985 A | 11/1993 | Nakanishi et al. .......... 252/180 |
| 5,264,136 A | 11/1993 | Howarth et al. ............. 210/754 |
| 5,264,229 A * | 11/1993 | Mannig et al. .............. 426/335 |
| 5,286,479 A | 2/1994 | Garlich et al. ................ 424/54 |
| 5,320,829 A | 6/1994 | Garlich et al. ................ 424/54 |
| 5,338,461 A | 8/1994 | Jones |
| 5,339,889 A | 8/1994 | Bigham |
| 5,384,102 A | 1/1995 | Ferguson et al. |
| 5,389,384 A | 2/1995 | Jooste ........................ 424/661 |
| 5,389,390 A * | 2/1995 | Kross ........................ 426/332 |
| 5,403,813 A | 4/1995 | Lichti et al. |
| 5,407,598 A | 4/1995 | Olson et al. ........... 252/186.35 |
| 5,409,711 A | 4/1995 | Mapelli et al. |
| 5,414,652 A | 5/1995 | Mieda et al. ................ 365/122 |
| 5,422,126 A | 6/1995 | Howarth et al. |
| 5,424,032 A | 6/1995 | Christensen et al. .......... 422/14 |
| 5,443,849 A | 8/1995 | Corby ........................ 424/667 |
| 5,460,833 A * | 10/1995 | Andrews et al. ............ 424/606 |
| 5,464,636 A | 11/1995 | Hight et al. ................. 424/661 |
| 5,476,116 A | 12/1995 | Price et al. |
| 5,484,615 A | 1/1996 | Kounev |
| 5,490,983 A | 2/1996 | Worley et al. .............. 424/405 |
| 5,490,992 A * | 2/1996 | Andrews et al. ............ 424/606 |
| 5,525,241 A | 6/1996 | Clavin et al. ............... 210/753 |
| 5,527,547 A | 6/1996 | Hight et al. ................. 424/661 |
| 5,565,109 A | 10/1996 | Sweeny ...................... 210/755 |
| 5,565,576 A | 10/1996 | Hall et al. |
| 5,578,559 A | 11/1996 | Dolan et al. |
| 5,589,106 A | 12/1996 | Shim et al. ................. 252/387 |
| 5,591,692 A | 1/1997 | Jones et al. |
| 5,603,941 A | 2/1997 | Farina et al. ............... 424/405 |
| 5,607,619 A | 3/1997 | Dadgar et al. ........... 252/187.2 |
| 5,610,126 A | 3/1997 | Barford et al. |
| 5,614,528 A | 3/1997 | Jones et al. |
| 5,622,708 A | 4/1997 | Richter et al. .............. 424/405 |
| 5,641,530 A | 6/1997 | Chen |
| 5,670,451 A | 9/1997 | Jones et al. |
| 5,670,646 A | 9/1997 | Worley et al. ........... 548/301.1 |
| 5,679,239 A | 10/1997 | Blum et al. ................. 205/556 |
| 5,683,654 A | 11/1997 | Dallmier et al. .............. 422/14 |
| 5,750,061 A | 5/1998 | Farina et al. |
| 5,753,602 A | 5/1998 | Hung et al. |
| 5,756,440 A | 5/1998 | Watanabe et al. |
| 5,763,376 A | 6/1998 | Ward et al. |
| 5,780,641 A | 7/1998 | Yerushalmi et al. |
| 5,795,487 A | 8/1998 | Dallmier et al. ............ 210/754 |
| 5,808,089 A | 9/1998 | Worley et al. ........... 548/318.5 |
| 5,821,546 A | 10/1998 | Xiao et al. |
| 5,830,511 A | 11/1998 | Mullerat et al. ............. 424/661 |
| 5,859,060 A | 1/1999 | Platt |
| 5,889,130 A | 3/1999 | Worley et al. .............. 526/261 |
| 5,891,499 A * | 4/1999 | Balsano ...................... 426/335 |
| 5,900,512 A | 5/1999 | Elnagar et al. ................ 568/14 |
| 5,902,818 A | 5/1999 | Worley et al. .............. 514/376 |
| 5,911,870 A | 6/1999 | Hough |
| 5,922,745 A | 7/1999 | McCarthy et al. .......... 514/372 |
| 5,932,265 A | 8/1999 | Morgan |
| 5,942,126 A | 8/1999 | Dallmier et al. ............. 210/756 |
| 5,942,153 A | 8/1999 | Heydel |
| 5,958,853 A | 9/1999 | Watanabe |
| 5,972,864 A | 10/1999 | Counts ...................... 510/192 |
| 5,981,461 A | 11/1999 | Counts et al. |
| 5,984,994 A | 11/1999 | Hudson |
| 6,004,587 A | 12/1999 | Mullerat et al. ............. 424/661 |
| 6,007,726 A | 12/1999 | Yang et al. ................. 210/752 |
| 6,007,735 A | 12/1999 | Creed .................... 252/186.25 |
| 6,015,782 A | 1/2000 | Petri et al. .................. 510/379 |
| 6,037,318 A | 3/2000 | Na et al. .................... 510/379 |
| 6,039,992 A | 3/2000 | Compadre et al. |
| 6,068,861 A | 5/2000 | Moore, Jr. et al. .......... 424/703 |
| 6,083,500 A | 7/2000 | Wooley et al. ........... 424/93.48 |
| 6,099,855 A | 8/2000 | Mullerat et al. ............. 424/442 |

| | | | |
|---|---|---|---|
| 6,110,353 A | 8/2000 | Hough | |
| 6,110,387 A | 8/2000 | Choudhury et al. | 210/752 |
| 6,123,870 A | 9/2000 | Yang et al. | 252/186.1 |
| 6,156,229 A | 12/2000 | Yang et al. | 252/186.1 |
| 6,172,040 B1 | 1/2001 | Naidu | 514/6 |
| 6,270,722 B1 | 8/2001 | Yang et al. | 422/37 |
| 6,284,144 B1 | 9/2001 | Itzhak | |
| 6,287,473 B1 | 9/2001 | Yang et al. | 210/754 |
| 6,299,909 B1 | 10/2001 | Moore, Jr. et al. | 424/703 |
| 6,306,441 B1 | 10/2001 | Moore, Jr. et al. | 424/703 |
| 6,322,822 B1 | 11/2001 | Moore, Jr. et al. | 424/703 |
| 6,342,528 B1 | 1/2002 | McKenzie et al. | |
| 6,348,227 B1 * | 2/2002 | Caracciolo, Jr. | 426/332 |
| 6,397,622 B1 | 6/2002 | Miller et al. | |
| 6,448,410 B1 | 9/2002 | Howarth et al. | |
| 6,495,698 B1 | 12/2002 | Howarth | |
| 6,508,954 B1 | 1/2003 | Elnagar et al. | |
| 6,565,868 B1 | 5/2003 | Howarth et al. | |
| 6,605,253 B1 * | 8/2003 | Perkins | 422/28 |
| 6,605,308 B2 * | 8/2003 | Shane et al. | 426/332 |
| 6,638,959 B2 | 10/2003 | Howarth et al. | |
| 6,680,070 B1 | 1/2004 | Howarth et al. | |

FOREIGN PATENT DOCUMENTS

| | | |
|---|---|---|
| GB | 1054243 | 1/1967 |
| GB | 1139188 | 1/1969 |
| GB | 1600289 | 10/1981 |
| GB | 2267487 | 12/1993 |
| GB | 2273106 | 6/1994 |
| JP | 56158333 | 12/1981 |
| JP | 7299468 | 11/1995 |
| WO | WO 8802987 | 5/1988 |
| WO | 8910696 | 11/1989 |
| WO | 9015780 | 12/1990 |
| WO | WO 96/28173 | 9/1996 |
| WO | WO 9630491 | 10/1996 |
| WO | WO 9715652 | 5/1997 |
| WO | 9720546 | 6/1997 |
| WO | 9720909 | 6/1997 |
| WO | 9734827 | 9/1997 |
| WO | WO 9743264 | 11/1997 |
| WO | 9743392 | 11/1997 |
| WO | 9804143 | 2/1998 |
| WO | 9815609 | 4/1998 |
| WO | 9906320 | 2/1999 |
| WO | 9932596 | 7/1999 |
| WO | 9955627 | 11/1999 |
| WO | 0034186 | 6/2000 |
| WO | WO 01/52827 A1 | 7/2001 |
| WO | WO 0153209 A2 | 7/2001 |
| WO | WO 01/53209 A2 | 7/2001 |

OTHER PUBLICATIONS

Frosti Abstract of Bocharov D.A., "Disinfection of Poultry Processing Plant Objects", Proceedings of the 22$^{nd}$ European meeting of Meat Research Workers, Malmo, Aug.–Sept., 1(C6), 4 pp., 1976. Accession No. 78674 Frosti.

Caplus Abstract of Heir, et al., The Staphylococcus qacH gene product: a new member of the SMR family encoding multidrug resistance, FEMS Microbiol. Lett. (1998), 163(1), ppg 49–56. Accession No. 1998:343309 CAPLUS.

Frosti Abstract of Lemaitre et al., "Plasmid–mediated resistance to antimicrobial agents among listeriae", Journal of Food Protection, Nov. 1998, 61 (11). ppg 1459–1464. Accession No. 483547 Frosti.

Frosti Abstract of Marriot, N.G., "Meat and poultry sanitation", Essentials of Food Sanitation, published by Chapman & Hall, London, 1997, 188–210. Accession No. 441637 Frosti.

Frosti Abstract of Mullerat et al., "Efficacy of Salmid, a sodium chlorite–based oxy–halogen disinfectant, to inactivate bacterial pathogens and extend shelf–life of broiler carcasses", Journal of Food Protection, 1994, 57(7), 596–603. Accession No. 353342 Frosti.

Caplus Abstract of Sanderson et al., "Case Reports: epidemic eye and upper respiratory imitation in poulrty proccessing plants", Appl. Occup. Environ. Hyg, 1995, 10(1), 43–9. Accession No. 1995:439186 CAPLUS.

Frosti Abstract of Sheldon, B.W., "New and novel chemical and biological approaches for inhibiting pathogens and spoilage microorganisms associated with muscle food systems", Turkeys, 1996, 44(2). 9–12. Accession No. 410383 Frosti.

Frosti Abstract of Smith, G., "Poultry industry looks to chlorine dioxide for pathogen control", Meat Processing, 1996, 35(10), 47. Accession No. 429057 Frosti.

Frosti Abstract of Sundheim, G., et al., "Resistance of meat associated staphylococci to a quatemary ammonium compound", Food Microbiology, 1992, 9(2). 161–7. Accession No. 291734 Frosti.

Frosti Abstract of "Foodborne Pathogen Control", Poultry International, Jul. 1994, 62, author unknown. Accession No. 359896 Frosti.

Carpentier et al., "Biofilms and their consequences, with particular reference to hygiene in the food industry", Journal of Applied Bacteriology, 1993, vol. 75, ppg 499–511.

Mora et al., "Properties of a New Chloramine Disinfectant and Detoxicant", Poultry Science, 1982, vol. 61, ppg 1968–1971.

Mantilla–Sandholm et al., "Biofilm Formation in the Industry: A Review", Food Reviews International, 8(4), 1992, ppg 573–603.

Smith et al., "Potential Uses of Combined Halogen Disinfectants in Poultry Processing", Poultry Science, 1990, vol. 69, ppg 1590–1594.

Williams, et al., "Research Note: Combined Halogen Disinfectants in Poultry Processing", Poultry Science, 1990, vol. 69, ppg 2248–2251.

Worley, et al., "The Stabilities of New N–halamine Water Disinfectants", Wat. Res. vol. 21(8), ppg 983–988,1987.

Blaser, Martin J., et al., "Inactivation of *Campylobacter jejuni* by Chlorine and Monochloramine", Applied and Environmental Microbiology, vol. 51, No. 2, 1986, ppg 307–311.

Carr, Anitra C., "Differential reactivities of hypochlorous and hypobromous acids with pruified *Escherichia coli Phospholipid*: formation of haloamines and halohydrins", Biochimica of Biophysica, 1392,1998, ppg 254–264.

Dickens, J.A., et al., "Efficacy of an Herbal Extract on the Microbiological Quality of Broiler During a Simulated Chill", Poultry Science, 2000, vol. 79, ppg 1200–1203.

Fabrizio, K.A., et al., "Comparison of Electrolyzed Oxidizing Water with Various Antimicorbial Interventions to Reduce Salmonella Species on Poultry", Poultry Science, 2000, vol. 81, ppg 1598–1605.

Hawkins, Clare L., et al., "Hypochlorite– and Hypobromite– Mediated Radical Formation and its Role in Cell Lysis", Archives of Biochemistry and Biophysics, vol. 395, No. 2, Nov. 15, 2001, ppg 137–145.

Kumar, Krishan, et al., "Kinetics and Mechanism of General–Acid–Assisted Oxidation of Bromide by Hypochlorite and Hypochlorus Acid", Inorg. Chem., 1987, vol. 26, ppg 2706–2711.

Lillard, H.S., "Effect of Trisodium Phosphate on Salmonellae Attached to Chicken Skin", Journal of Food Protection, vol. 57, No. 6, Jun. 1994, ppg 465–469.

Mead, G.C., et al., "The Effectiveness of in–plant Chlorination in Poultry Processing", Mr. Poult. Sci., vol. 16, 1975, ppg 517–526.

Northcult, J.K. et al., "Effect of Broiler Age, Feed Withdrawal, and Transportation on Levels of Coliforms, Campylobacter, Escherichia coli and Salmonella on Carcasses Before and After", Poultry Science, 2003, vol. 82, ppg 169–173.

Patterson, J.T., "Chlorination of Water Used for Poultry Processing", British Poultry Science, vol. 9, part 2, 1968, ppg 129–133.

"9215 C. Spread Plate Method", Microbiological Examination (9000), ppg 9–38–9–40.

Tamblyn, K.C., et al., "Utilization of the Skin Attachment Model to Determine the Antibacterial Efficacy of Potential Carcass Treatments", Poultry Science, 1997, vol. 76, ppg 1318–1323.

Tsai, Lee–Shin, et al., "Chlorination of Poultry Chiller Water: Chlorine Demand and Disinfection Efficiency", Poultry Science, 1992, vol. 71, ppg 188–196.

"Pathogen Reduction; Hazard Analysis and Critical Control Point (HACCP) Systems; Final Rule", Federal Register, Jul. 25, 1996, vol. 61, No. 144, p. 38806–38814 and 38854–38855.

Vissers, Margret C.M., et al., "Comparison of human red cell lysis by hypochlorous and hypobromous acids: Insights into the mechanism of lysis", Biochem. J., vol. 330, 1998, ppg 131–138.

Vissers, Margret C.M., et al., "Fatty acid chlorohydrins and bromohydrins are cytotoxic to human endothelial cells", Redox Report, vol. 6, No. 1, 2001, ppg 49–55.

Wabeck, Charles J., "Methods to Reduce Microorganisms on Poultry", Broiler Industry, Dec. 1994, ppg 34, 36, 38, 40, 42.

Yang, Hong, et al., "Survival and Death of Salmonella Typhimurium and Campylobacter jejuni in Processing Water and on Chicken Skin during Poultry Scalding and Chilling", Journal of Food Protection, vol. 64, No. 6, 2001, ppg 770–776.

Corral et al., "Substitution in the Hydantoin Ring. III. Halogenation", J. Org. Chem., 1963, vol. 28, pp. 1100–1104.

Jolles, "General Methods of Bromination", Bromine and its Compounds, 1966, Ernest Benn, London, pp. 365.

Markish et al., "New Aspects on the Preparation of 1,3–Dibromo–5,5–Dimethylhydantoin", Ind. Eng. Chem. Res. 1995, vol. 34, pp. 2125–2127.

Orazi et al., "Halogenacion con 3–Bromo–5,5–Dimetil–Hidantoina", Anales Assoc. Quim. Argentina, 1949, vol. 37, pp. 192–196. (Not translated).

Orazi et al., "Halogenacion Con 1–3–Dibromo–5,5–Dimetil–Hidantoina", Anales Assoc. Quim. Argentina, 1950, vol. 38, pp. 5–11. (Not translated).

Gottard: Reaction of Cl Br –In Aqueous solution (76 Zeutralks. Baktreiol., Parasiteukd,) In Fektionskr. Hyg., Abt. 1; Orig., Geihe B 162 (3–4), pp. 384–388.

HCAPLUS Abstract of JP 07171576 A2 issued 1995.

HCAPLUS Abstract of JP 07277912 A2 issued 1995.

HCAPLUS Abstract of JP 08027119 A2 issued 1996.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, pp. 1385–1389.

Krycer et al., "An Evaluation of Tablet Binding Agents Part II. Pressure Binders", Powder Technology, 1983, vol. 34, pp. 53–.

Petterson, "N–Halogen Compounds. I. Decomposition of 1,3–Dichloro–5,5–dimethylhydantoin in Water at pH 9", J. Org. Chem., 1959, vol. 24, pp. 1414–1419.

HCAPLUS Abstract of JP 08239699 A2 issued 1996.

HCAPLUS Abstract of JP 09087684 A2 issued 1997.

HCAPLUS Abstract of JP 09227317 A2 issued 1997.

Hayward America's #1 Pool Water Systems Product Catalog, "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?item1D=61>, 2 pages.

Author unknown, "Big Brother Brominator –Brominators", Bulky Systems Website, <http://www.bulkysystemsinc.com/brominator.html> (Visited Aug. 10, 2001). 1 page.

Hayward Pool Products Owner's Guide, Installation and Operating Instructions, "Hayward Chemical Feeder", Models C250CF, C500CF, C1100CF, C1800CF, C2400CF, – 1998 –4 pages.

Hayward America's #1 Pool Water Systems Product Catalog, "Automatic Chemical Feeders" Chlorinators (Slow Dissolve Tri–Chlor Only) and Brominators, Buyers Guide, Hayward Pool Products Inc., Website, <http://www.haywardnet.com/products/catalog/displayProdInfo.cfm?itemID=60>,2 p.

Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.

Pentair Pool Products Brochure, "Rainbow Model 300 Automatic Chlorine/Bromine Off–line Feeders", "The Efficient, Easy Way to Sanitize Your Pool or Spa", date unknown, 1 page.

Pentair Pool Products Brochure, "Rainbow Model 320 Automatic Chlorine/Bromine In–line Feeder", "Saves Time, Reduces Manual Handling of Chemicals", date unknown, 7 pages.

Sani–King Perform–Max Pool Sanitizer Instruction Guide, Models 910, 940, & 980 (Inline) and Models 930 & 960 (Off–line), date unknown, 16 pages.

Sani–King Spa Feeder Product Brochure Model 740 from King Technology Website, <http://www.kingtechnology.com/spafeeder.htm> Visited (Aug. 10, 2001), 2000, 4 pages.

Sani–King Adjust–A–Flo Product Brochure from King Technology Website <http://www.kingtechnology.com/spafeeder.htm> (Visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Product Brochure Model 910 & 930 from King Technology Website.

Discount Pool & Spa Supplies, Automatic Chlorinators and Chemical Feeders Website, <http://www.discountpoolsupplies.com/Chemfeeders/> Visited Aug. 10, 2001, 3 pages.

Sorum —Fundamentals of General Chemistry, p. 315, 1955.

Al Zahrani, S.M., "Utilization of Polyethylene and Paraffin Waxes as Controlled Deliveery Systems for Different Fertilizers", Ind. Eng. Chem. Res., 2000, vol 39, pp 369–371.

* cited by examiner

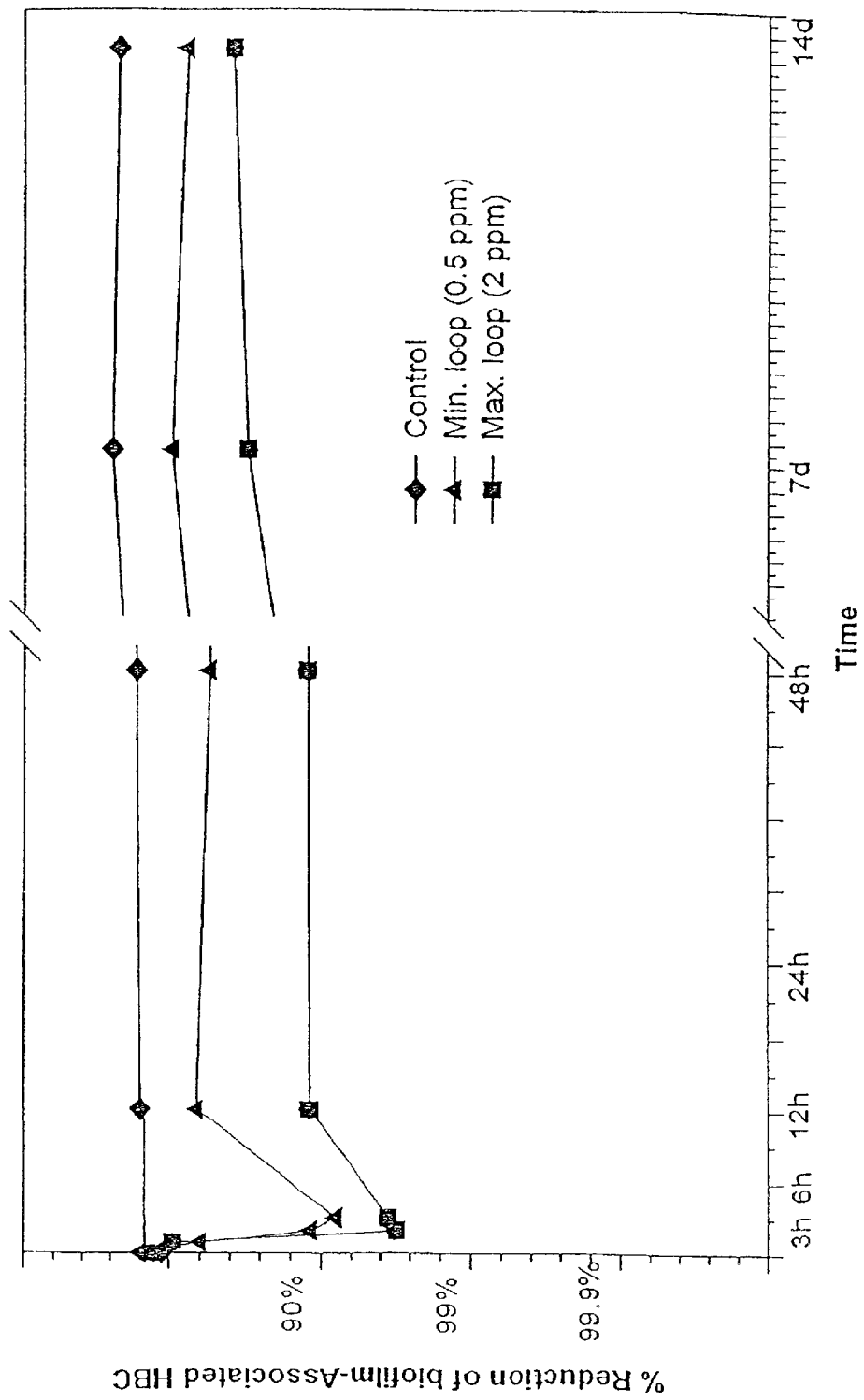
Figure 5 Efficacy of Stabrom 909 in Eradicating Biofilm-Associated HPC

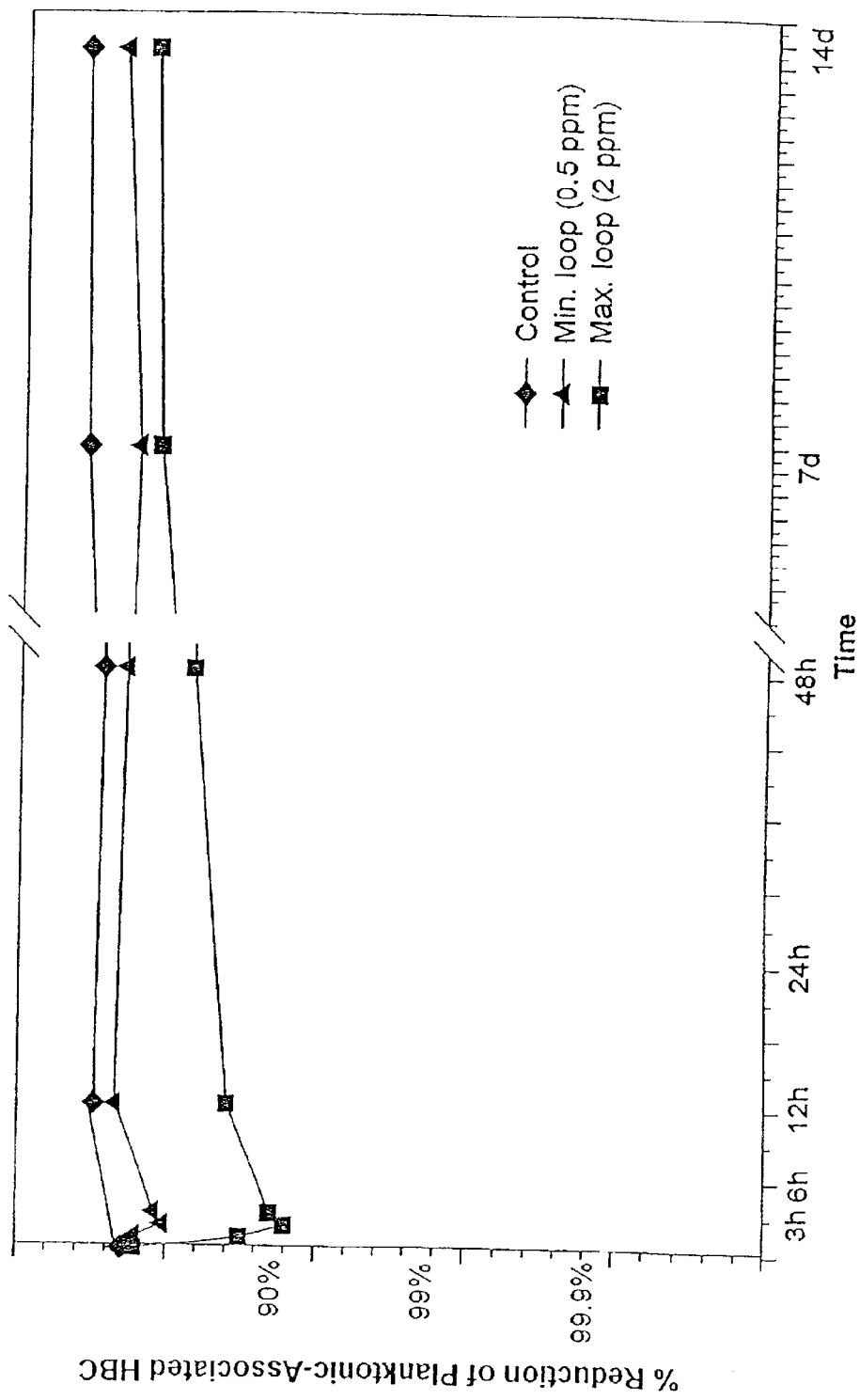

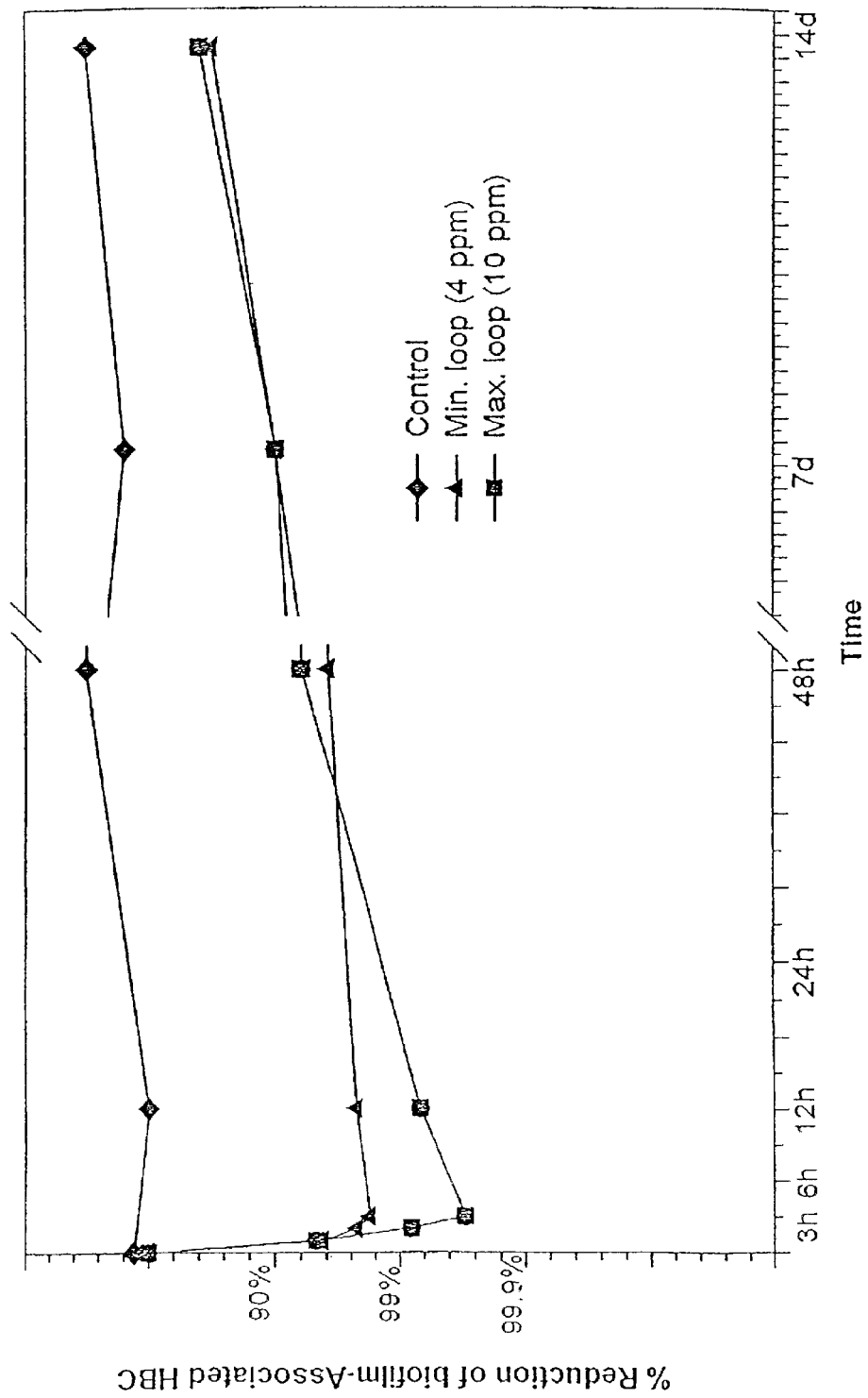

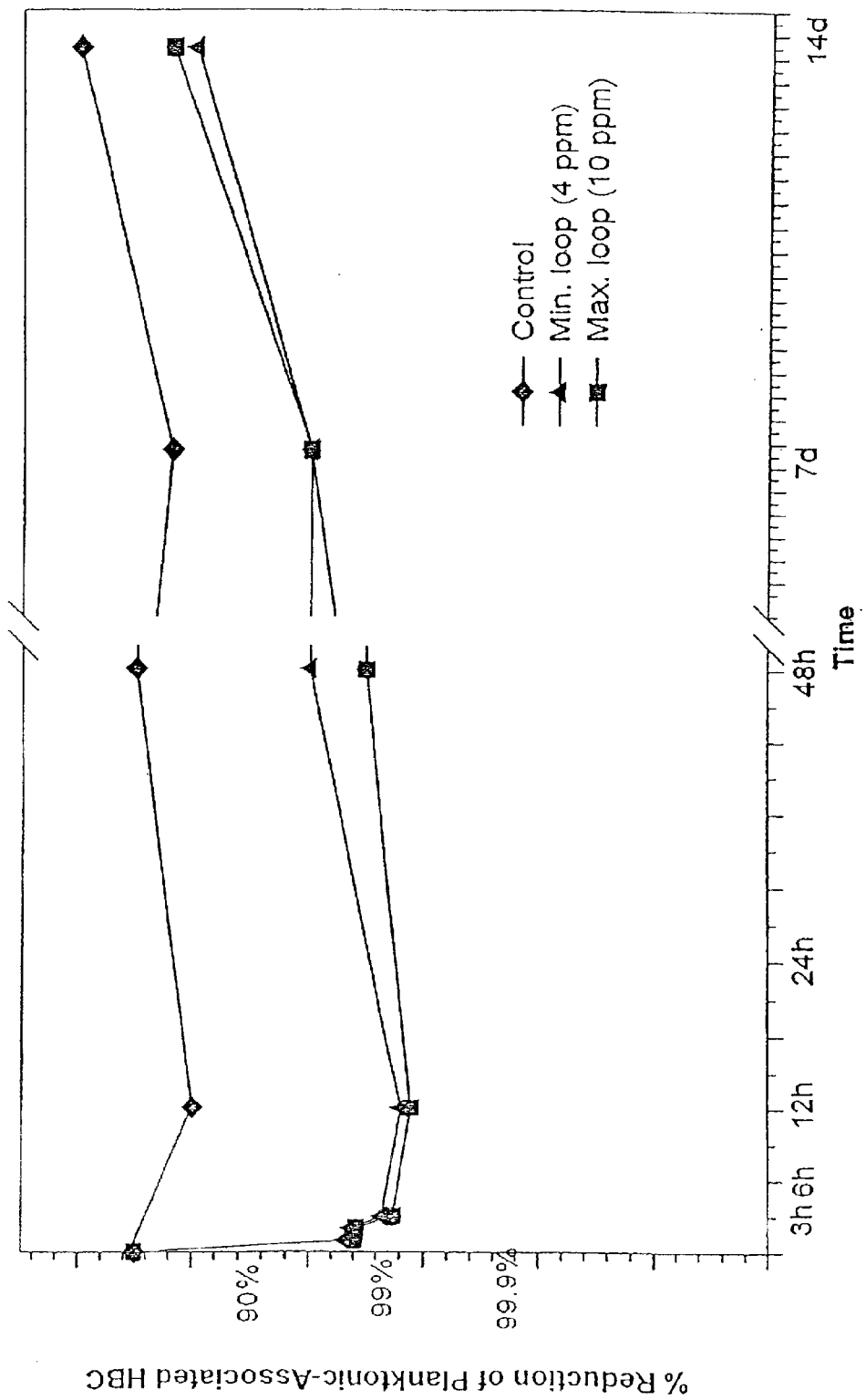

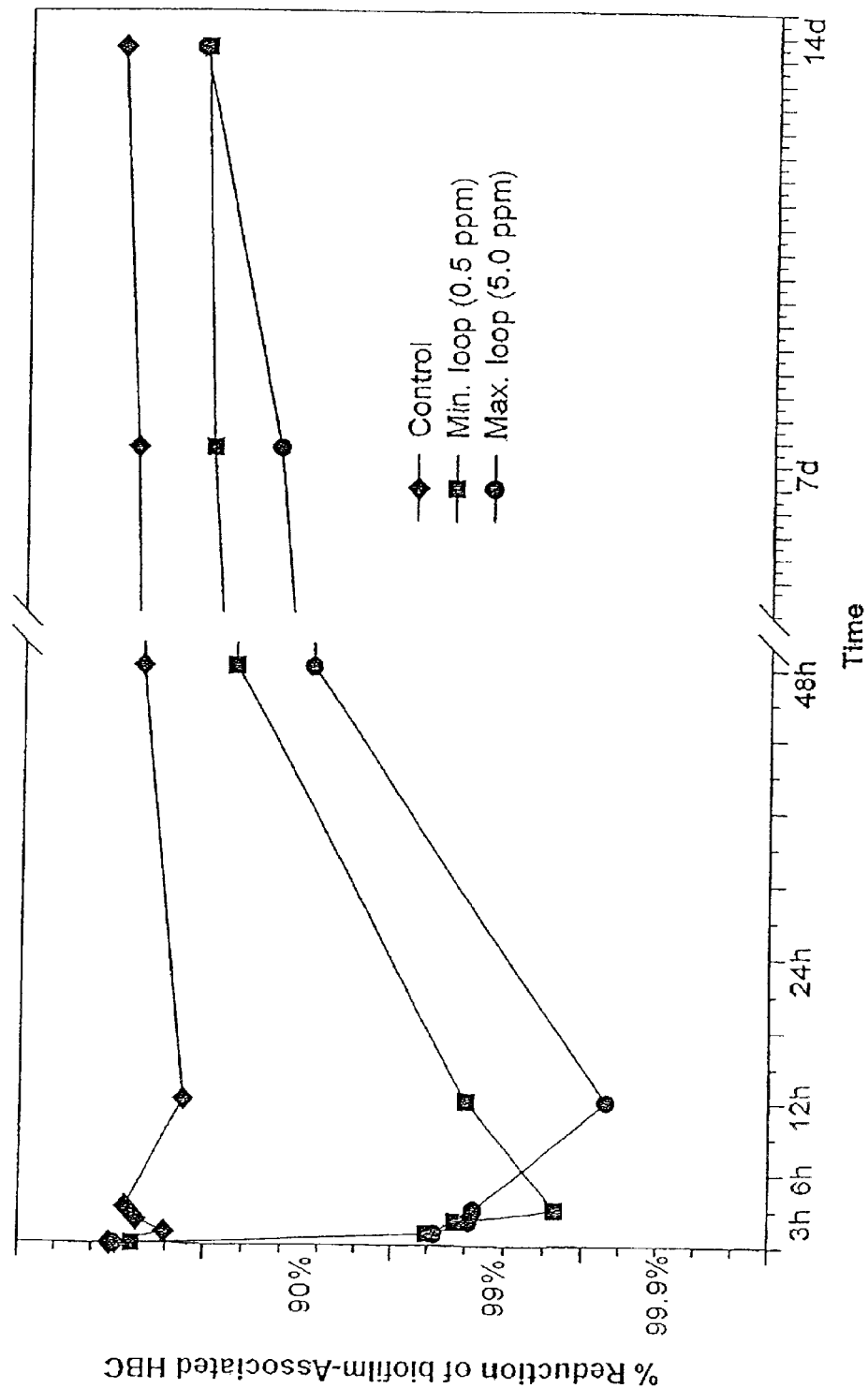

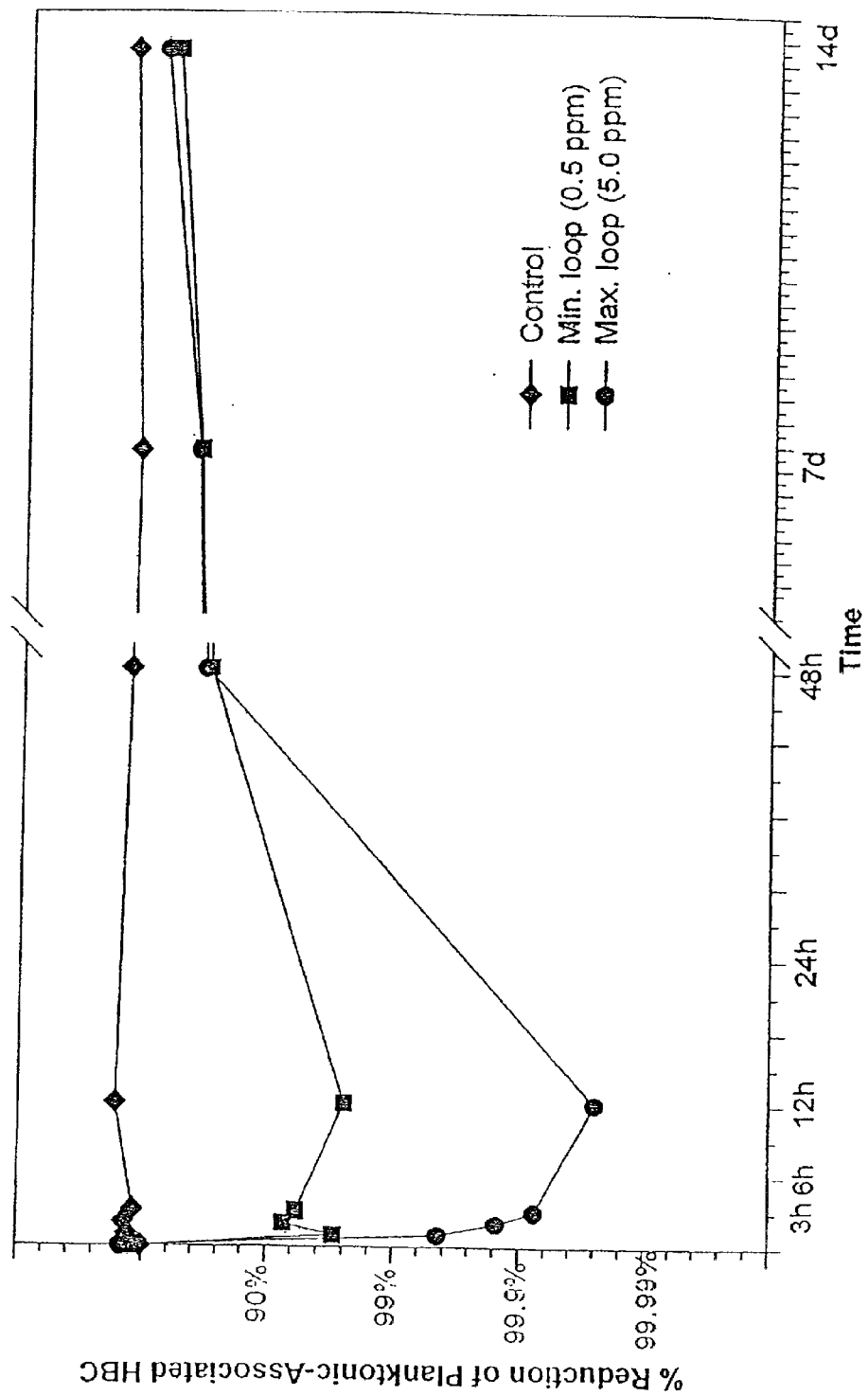

US 6,908,636 B2

MICROBIOLOGICAL CONTROL IN POULTRY PROCESSING

REFERENCE TO RELATED APPLICATION

This is a continuation-in-part of commonly-owned application Ser. No. 09/893,581, filed Jun. 28, 2001 now abandoned.

REFERENCE TO OTHER COMMONLY-OWNED APPLICATIONS

Reference is hereby made to the following commonly-owned applications: application Ser. No. 09/088,300, filed Jun. 1, 1998, now U.S. Pat. No. 6,068,861 issued May 30, 2000; application Ser. No. 09/296,499, filed Apr. 22, 1999, now U.S. Pat. No. 6,110,387 issued Aug. 29, 2000; application Ser. No. 09/323,348, filed Jun. 1, 1999, now U.S. Pat. No. 6,303,038 B1 issued Oct. 16, 2001; application Ser. No. 09/404,184, filed Sep. 24, 1999; application Ser. No. 09/442,025, filed Nov. 17, 1999, now U.S. Pat. No. 6,306,441 issued Oct. 23, 2001; application Ser. No. 09/451,319, filed Nov. 30, 1999; application Ser. No. 09/451,344, filed Nov. 30, 1999, now U.S. Pat. No. 6,352,725 B1 issued Mar. 5, 2002; application No. 09/456,781, filed Dec. 8, 1999, now U.S. Pat. No. 6,495,169 B1 issued Dec. 17, 2002; application Ser. No. 09/483,896, filed Jan. 18, 2000, now U.S. Pat. No. 6,448,410 B1 issued Sep. 10, 2002; application No. 09/484,687, filed Jan. 18, 2000, now U.S. Pat. No. 6,508,954 B1 issued Jan. 21, 2003; application No. 09/484,844, filed Jan. 18, 2000; application Ser. No. 09/484,891, filed Jan. 18, 2000 now U.S. Pat. No. 6,495,698 B1 issued Dec. 17, 2002; application Ser. No. 09/484,938, filed Jan. 18, 2000, now U.S. Pat. No. 6,565,868 B1 issued May 20, 2003; application No. 09/487,816, filed Jan. 18, 2000; application Ser. No. 09/506,911, filed Feb. 18, 2000, now U.S. Pat. No. 6,511,682 B1 issued Jan. 28, 2003; application Ser. No. 09/658,839, filed Sep. 8, 2000, now U.S. Pat. No. 6,375,991 B1 issued Apr. 23, 2002; application No. 09/663,788, filed Sep. 18, 2000, now U.S. Pat. No. 6,348,219 B1 issued Feb. 19, 2002; application Ser. No. 09/663,948, filed Sep. 18, 2000, now U.S. Pat. No. 6,299,909 B1 issued Oct. 9, 2001; application Ser. No. 09/732,601, filed Dec. 7, 2000, now U.S. Pat. No. 6,506,418 B1 issued Jan. 14, 2003; application Ser. No. 09/775,516, filed Feb. 2, 2001, now U.S. Pat. No. 6,641,828 B1 issued Nov. 4, 2003; application No. 09/778,228, filed Feb. 6, 2001, now abandoned; application Ser. No. 09/785,890, filed Feb. 16, 2001; application Ser. No. 09/893,581, filed Jun. 28, 2001, now abandoned; and application Ser. No. 09/974,622, filed Oct. 9, 2001, now U.S. Pat. No. 6,652,889 B2 issued Nov. 25, 2003.

REFERENCE TO A PREVIOUSLY JOINTLY-OWNED APPLICATION

Reference is hereby made to Application No. 10/028,631, filed Dec. 21, 2001, which is presently owned by the other of the original joint owners.

BACKGROUND

Poultry processing is an area in which microbiological control is of vital importance. By the very nature of the processing involved there are numerous opportunities for the poultry to be exposed to various pathogens in the form of mobile bacteria such as for example *Escherichia coli, Salmonella enteritidis, Salmonella typhimurim, Campylobacter jejuni, Campylobacter coli, Campylobacter lari,* and in the form of biofilms such as for example *Listeria monocytogenes, Pseudomonas fluorescens, Pseudomonas aeruginosa, Enterococcus faecium,* and *Staphylococcus aureus.* The thought of handling, processing and consuming bacteria-infested poultry is revolting in the extreme.

Heretofore certain chlorine-based microbiocides have been proposed and used in an attempt to provide suitable sanitation in connection with poultry processing. Unfortunately while some chlorine-based microbiocides show some effectiveness, they possess a number of serious shortcomings. For one thing they are not as effective as one might wish. Secondly, they tend to be odorous and in many cases can exert a bleaching effect upon the poultry carcasses which can prove unpalatable to the consumer. Moreover, because of the spread of fecal matter associated with the evisceration of the fowl, fecal bacteria abound. This egregious condition in turn results in high nitrogen levels in the wash waters, and on wet surfaces such as cutting surfaces, conduits, tank surfaces, and other downstream equipment exposed one way or another to these wash waters. Unfortunately, the active chlorine species of certain chlorine-based microbiocides tend to react with the nitrogenous species to form chloroamines which are lachrymators as well as being corrosive to metallic surfaces. In fact, as little as 50 ppm of chlorine in aqueous washing tanks containing nitrogenous impurities can produce quantities of air-borne lachrymators that are intolerable to plant workers. Furthermore, the consumption of chlorine values in forming chloramines results in a significant loss of biocidal effectiveness inasmuch as the chloroamines are not biocidally-active species.

Clearly therefore a need exists for anew, more effective, economically feasible way of providing microbiological control in the poultry processing industry.

BRIEF SUMMARY OF THE INVENTION

This invention fulfills the foregoing need by providing and utilizing in certain highly effective halogen-based microbiocides in the processing of poultry and in the disinfection of equipment, instruments, apparatus, and/or water used in the processing of poultry, and/or of carcasses and/or parts of poultry resulting from the processing of poultry. Microbiocidal agents used pursuant to this invention can be produced economically in straightforward processing from relatively low cost raw materials and because of their effectiveness, can provide microbiological control on an economical basis consistent with the needs of the industry.

In one of its embodiments this invention provides in the processing of poultry, the improvement which comprises disinfecting equipment, instruments, apparatus and/or water used in such processing, and/or carcasses and/or other parts of poultry resulting from such processing, with a halogen-based microbiocide which is:

(I) an aqueous microbiocidal solution of one or more active halogen species, which solution is a derivative product in an aqueous medium of (a) bromine, chlorine, or bromine chloride, or any two or all three thereof, and (b) a water-soluble source of sulfamate anion; or (II) an aqueous microbiocidal solution of one or more active halogen species, which solution is a derivative product in an aqueous medium of at least one 1,3-dihalo-5,5-dialkylhydantoin in which one of the halogen atoms is a chlorine atom and the other is a chlorine or bromine atom, and in which each of the alkyl groups, independently, contains in the range of 1 to about 4 carbon atoms; or (III) an aqueous microbiocidal solution of one or more active halogen species, which solution is a derivative product in an aqueous medium of at least one 1,3- dibromo-5,5-dialkylhydantoin in which one of the alkyl groups is a methyl group and the other alkyl group contains in the range of 1 to about 4 carbon atoms: or (IV) any two or more of (I), (II), and (III).

The derivative product of (I) above is an aqueous microbiocidal solution ofone or more active halogen species, which solution is formed by and thus results from a reaction in water between bromine, chlorine, or bromine chloride, or any two or all three thereof, and a water-soluble source of sulfamate anion. A concentrated solution of this type containing over 100,000 ppm of active halogen is available commercially from Albemarle Corporation under the trademark STABROM® 909 biocide. A concentrated solution such as this can be applied to equipment, instruments, or apparatus used in poultry processing and added to water used in poultry processing with or without first being further diluted with water. On the other hand, such a concentrated solution should be diluted with or in water before application to poultry carcasses or parts thereof, such as by addition of the concentrate to water in a chilling tank or the like. Similarly, the derivative products of (II) and (III) above are aqueous microbiocidal solutions of one or more active halogen species, which solutions are formed by and thus result from dissolving the specified 1,3-dihalo-5,5-dialkylhydantoin(s) in water. Such 1,3-dihalo-5,5-dialkylhydantoins are typically available commercially in the form of solids and concentrated aqueous solutions can be formed from such solids for application with or without further dilution to equipment, instruments, or apparatus used in poultry processing and added to water used in poultry processing. But for application to poultry carcasses or parts thereof, either the concentrated solution should be further diluted with waterbefore use, or the selected 1,3-dihalo-5,5-dialkylhydantoin solids should be added to water in proportions yielding the desired microbiocidal dosage directly without forming an intermediate more concentrated solution.

Purely for convenience, the microbiocides of (I) described above when made from bromine chloride, bromine and chlorine, or bromine, chlorine, and bromine chloride, and a sulfamate source, are sometimes referred to hereinafter as "sulfamate-stabilized bromine chloride" even though technically the actual chemical species in the aqueous medium are most probably not bromine chloride molecules or sulfamate adducts or complexes of bromine chloride. Thus the designation "sulfamate-stabilized bromine chloride" is simply a shorthand way of referring to such compositions, and the designation does not signify, suggest, or imply anything about the actual chemical structure of the composition.

In preferred embodiments, the halogen-based microbiocide used in the above process is (A) abromine-based microbiocide comprising an overbased aqueous microbiocidal solution of one or more active bromine species, said species resulting from a reaction in water between bromine or bromine chloride, a mixture of bromine chloride and bromine, or a combination of bromine and chlorine in which the molar amount of chlorine is either equivalent to the molar amount of bromine or less than the molar amount of bromine, and a water-soluble source of sulfamate anion, or (B) an aqueous microbiocidal solution of at least one 1,3-dibromo-5,5-dialkylhydantoin in which one of the alkyl groups is a methyl group and the other alkyl group contains in the range of 1 to about 4 carbon atoms, or (C) both of (A) and (B) hereof. Thus in the embodiments of this invention wherein equipment, instruments, apparatus and/or water used in poultry processing is disinfected, and/or carcasses and/or other parts of poultry resulting from such processing are disinfected, "bromine-based" means any of the microbiocides referred to in this paragraph as (A), (B), or (C). In practice, the surfaces to be disinfected are contacted with the aqueous microbiocidal solutions of (A), (B), or (C) which of course contain amicrobiocidally-effective amount of the microbiocidal agent and/or microbiocidal hydrolysis product(s) thereof.

Such bromine-based microbiocides are more effective than chlorine-based microbiocides against various bacteria and biofilms. In addition, these bromine-based microbiocides tend to be less odorous than chlorine-based microbiocides, and are essentially devoid of unwanted bleaching activity. Moreover, while some of the bromine-based microbiocides may possibly react with nitrogenous species, such as are present in water and on surfaces associated with poultry processing, the resultant bromamines would also possess microbiological activity. Thus such side reactions would not materially decrease the microbiological effectiveness made available to the poultry processor by use of these bromine-based microbiocides. Furthermore, bromamines generally do not exhibit obnoxious properties toward workers in the processing plant whereas chloramines resulting from use of certain chlorine-based microbiocides under the same conditions tend to be powerful lachrymators.

As noted above, the halogen-based microbiocides of (I) above are microbiocidal solutions of one or more active halogen species, which solutions are derivative products in a aqueous medium such as water of bromine, chlorine, or bromine chloride, or any two or all three thereof and a water-soluble source of sulfamate anion. Likewise, the preferred bromine-based microbiocides of (A) above are microbiocidal solutions of one or more active bromine species, which solutions are derivative products in a aqueous medium such as water of bromine or bromine chloride, a mixture of bromine chloride and bromine, or a combination of bromine and chlorine in which the molar amount of chlorine is either equivalent to the molar amount of bromine or less than the molar amount of bromine, and a water-soluble source of sulfamate anion. To form these derivative products the components from which the derivative products are formed are brought together in an aqueous medium such as water, which medium or water, when forming the product, preferably is always at a pH of at least 7 and more preferably is always at a pH higher than 7, e.g., in the range of 10–14, by use of an inorganic base such as sodium hydroxide. When using a commercially-available product of this type (Stabrom® 909 biocide; Albemarle Corporation), the pH of the aqueous product as received is normally in the range of 13 to 14.

Similarly, the halogen-based microbiocides of (II) above are microbiocidal solutions of one or more active halogen species, which solutions are derivative products in an aqueous medium such as water of at least one 1,3-dihalo-5,5-dialkylhydantoin in which one of the halogen atoms is a chlorine atom and the other is a chlorine or bromine atom and the akyls are as described. Of the halogen-based microbiocides of (II) above, preferred are microbiocidal solutions of one or more active halogen species, which solutions are derivative products in an aqueous medium such as water of at least one 1,3-dihalo-5,5-dialkylhydantoin in which one of the halogen atoms is a bromine atom and the other is a chlorine atom (and the alkyls are as described). The bromine-based microbiocides of (III) above and of (B) above are microbiocidal solutions of one or more active bromine species, which solutions are derivative products in an aqueous medium such as water of at least one 1,3- dibromo-5,5-dialkylhydantoin in which the alkyls are as described. Upon dissolving in an aqueous medium such as water a 1,3-dihalo-5,5-dialkylhydantoin referred to in this paragraph, a transformation takes place so that active halogen (or bromine) species are present in the resultant solution.

The aqueous microbiocidal solutions used pursuant to the above embodiments of this invention can be formed in many cases by adding the microbiocidal agent itself (i.e., in undiluted form) or as a preformed concentrated aqueous solution thereof to water being used in one or more poultry processing operations (e.g., water flowing into chill tanks, or water already in chill tanks, etc.) to form a diluted microbiocidal solution of this invention which contacts the surfaces to be disinfected. Alternatively, a concentrated preformed aqueous solution of the microbiocidal agent can be applied directly to the surfaces to be disinfected (e.g., surfaces of cutting tables, or knives, or etc.), or more usually such concentrated solution would be mixed with water to form a more dilute solution of the microbiocidal agent which is applied to the surfaces to be disinfected and/or introduced into water being used in poultry processing operations. In short, the aqueous microbiocidal solutions used pursuant to these embodiments of the invention can be made in whole or in part from water already in use or to be used in the poultry processing operations, or can be made entirely from water separate from that used or to be used in the poultry processing. In each such case, the contacting of the aqueous microbiocidal solution however produced and/or applied to the surfaces results in effective disinfection.

At present the most preferred bromine-based microbiocide used in the practice of any embodiment of this invention is a water-soluble 1,3-dibromo-5,5-dialkylhydantoin in which one of the alkyl groups is a methyl group and the other is an alkyl group containing from 1 to about 4 carbon atoms, with 1,3-dibromo-5,5-dimethylhydantoin being the most preferred of all.

Various embodiments and features of this invention will be still further apparent from the ensuing description and appended claims.

BRIEF DESCRIPTION OF THE DRAWINGS

FIGS. 5 and 6 are graphical depictions of the results obtained in tests involving use of bromine species derived from sulfamate-stabilized bromine chloride in eradicating HPC (heterotrophic plate count) bacteria in biofilm and in planktonic form, respectively, at concentrations in water of 0.5 ppm and 2 ppm as bromine.

FIGS. 7 and 8 are graphical depictions of the results obtained in tests involving use of bromine species derived from sulfamate-stabilized bromine chloride in eradicating HPC (heterotrophic plate count) bacteria in biofilm and in planktonic form, respectively, at concentrations in water of 4 ppm and. 10 ppm as bromine.

FIG. 9 is a graphical depiction of the results obtained in tests involving use of bromine species derived from 1,3-dibromo-5,5-dimethylhydantoin in eradicating HPC (heterotrophic plate count) bacteria in a bioflim at concentrations in water of 0.5 and 5 ppm as bromine.

FIG. 10 is a graphical depiction of the results obtained in tests involving use of bromine species derived from 1,3-dibromo-5,5-dimethylhydantoin in eradicating planktonic HPC (heterotrophic plate count) bacteria at concentrations in water of 0.5 and 5 ppm as bromine.

FURTHER DETAILED DESCRIPTION OF THE INVENTION

Figure 1:
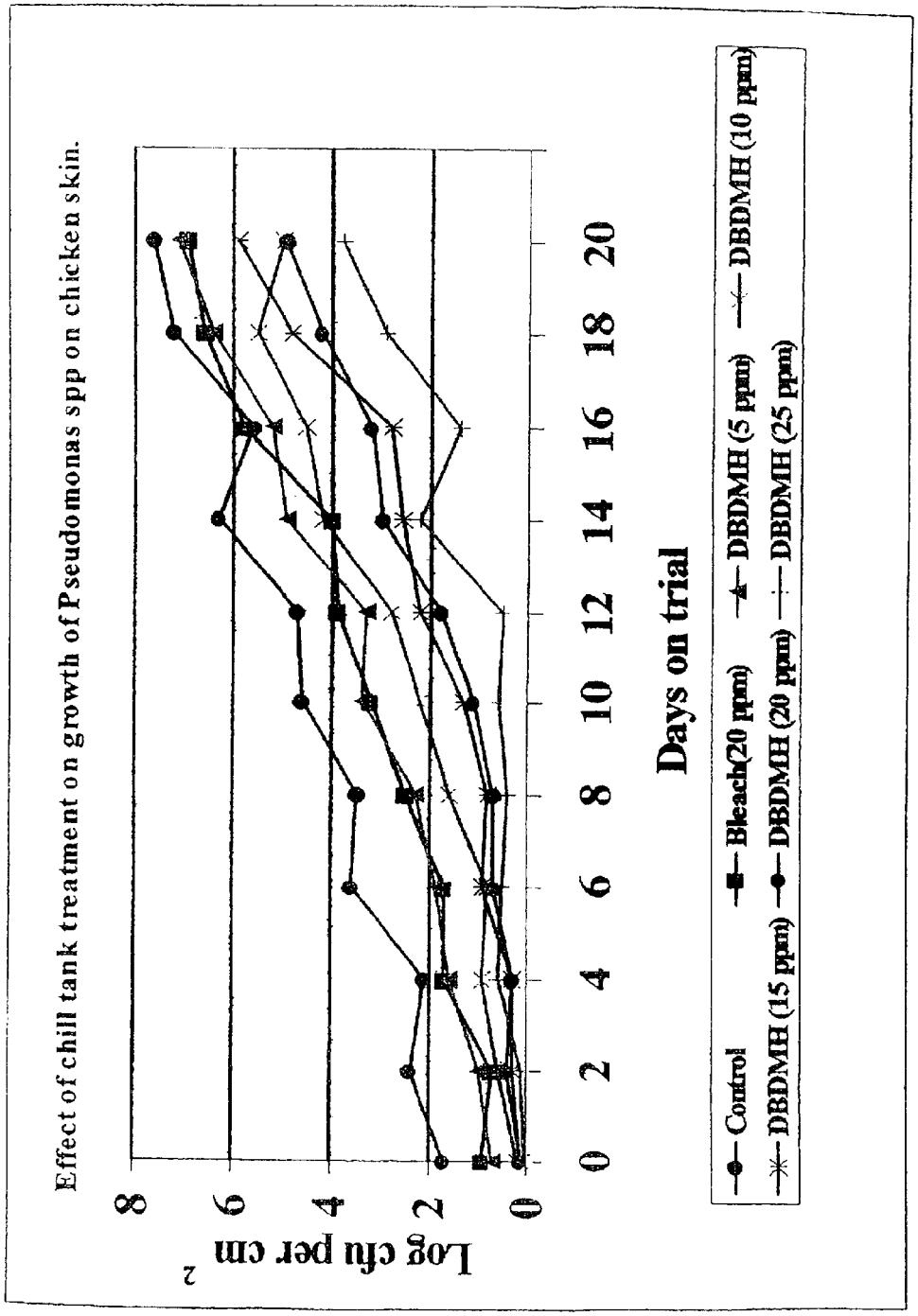
FIG. 1 is a graphical depiction of the effect of chill tank microbiocidal treatments on growth of Pseudomonas species on chicken skin.

One group of halogen-based microbiocides for use in disinfection of equipment, instruments, apparatus, and/or water used in the processing of poultry, and/or of carcasses and/or parts of poultry resulting from the processing of poultry pursuant to this invention is an aqueous microbiocidal solution of one or more active halogen species, said species resulting from a reaction in water between bromine, chlorine, or bromine chloride, or any two or all three thereof, and a water-soluble source of sulfamate anion. If sulfamic acid is used in forming this microbiocide, the solution should also be provided with a base, preferably enough base to keep the solution alkaline, i.e., with a pH above 7, preferably above about 10 and most preferably about 13 or above. The lower the pH, the more unstable the solution, and thus if the solution is prepared on site for immediate use, the use of a base is not essential. However, it is preferable to employ a concentrated microbiocidal solution manufactured elsewhere, and in such case the concentrated solution would be provided as an overbased solution with a pH of, say, about 13 or more. Often such concentrated solutions will contain over 50,000 ppm (wt/wt) of active halogen, preferably at least about 100,000 ppm (wt/wt) of active halogen, and sometimes as much as about 150,000 ppm (wt/wt) or more of active halogen, active halogen content being determinable by use of conventional starch-iodine titration.

One preferred group of this type is a bromine-based microbiocidal solution formed by reacting bromine or, more preferably bromine chloride, a mixture of bromine chloride and bromine, or a combination of bromine and chlorine in which the molar amount of chlorine is either equivalent to the molar amount of bromine or less than the molar amount of bromine, in an aqueous medium with sulfamic acid and/or a water-soluble salt of sulfamic acid. Except when made on site for immediate use, such solutions should be highly alkaline solutions typically with a pH of at least about 12 and preferably at least about 13, such pH resulting from use of a base such as sodium hydroxide or the like, in producing the solution. Concentrated solutions of this type are available in the marketplace, for example, Stabrom® 909 biocide (Albemarle Corporation). Processes for producing these concentrated aqueous microbiocidal solutions are described in commonly-owned U.S. Pat. No. 6,068,861, issued May 30, 2000, and 6,299,909 B1, issued Oct. 9, 2001, all disclosures of which are incorporated herein by reference.

It will be appreciated that even where the microbiocide is made from bromine chloride, a mixture of bromine chloride and bromine, or a combination of bromine and chlorine in which the molar amount of chlorine is either equivalent to the molar amount of bromine or less than the molar amount of bromine is used, the microbiocide is bromine-based as most of the chlorine usually winds up as a chloride salt such as sodium chloride since an alkali metal base such as sodium hydroxide is typically used in the processing to raise the pH of the product solution to at least about 13. Thus the chlorine in the product solution is not present as a significant microbiocide.

Another group of halogen-based microbiocides for use in these embodiments of this invention is one or more N,N'-halo-5,5-dialkylhydantoins in which one of the halogen atoms is chlorine and the other is bromine or chlorine, and in which the alkyl groups, independently, each contain from 1 to about 4 carbon atoms. Suitable compounds of this type include, for example, such compounds as 1,3-dichloro-5,5-dimethylhydantoin, 1,3-dichloro-5,5-diethylhydantoin, 1,3-dichloro-5,5-di-n-butylhydantoin, 1,3-dichloro-5-ethyl-5-methylhydantoin, N,N'-bromochloro-5,5-dimethylhydantoin, N,N'-bromochloro-5-ethyl-5-methylhydantoin, N,N'-bromochloro-5-propyl-5-methylhydantoin, N,N'-bromochloro-5-isopropyl-5-methylhydantoin, N,N'-bromochloro-5-butyl-5-methylhydantoin, N,N'-bromochloro-5-isobutyl-5-methylhydantoin, N,N'-bromochloro-5-sec-butyl-5-methylhydantoin, N,N'-bromochloro-5-tert-butyl-5-methylhydantoin, N,N'-bromochloro-5,5-diethylhydantoin, and mixtures of any two or more of the foregoing. N,N'-bromochloro-5,5-dimethylhydantoin is available commercially under the trade designation Bromicide® biocide (Great Lakes Chemical Corporation). Another suitable bromochlorohydantoin mixture is composed predominantly of N,N'-bromochloro-5,5-dimethylhydantoin together with a minor proportion by weight of 1,3-dichloro-5-ethyl-5-methylhydantoin. A mixture of this latter type is available in the marketplace under the trade designation Dantobrom® biocide (Lonza Corporation).

When a mixture of two or more of the foregoing N,N'-bromochloro-5,5-dialkylhydantoin biocides is used pursuant to this invention, the individual biocides of the mixture can be in any proportions relative to each other.

It will be understood that the designation N,N' in reference to, say, N,N'-bromochloro-5,5-dimethylhydantoin means that this compound can be (1) 1-bromo-3-chloro-5,5-dimethylhydantoin, or (2) 1-chloro-3-bromo-5,5-dimethylhydantoin, or (3) a mixture of 1-bromo-3-chloro-5,5-dimethylhydantoin and 1-chloro-3-bromo-5,5-dimethylhydantoin. Also, it is conceivable that some 1,3-dichloro-5,5-dimethylhydantoin and 1,3-dibromo-5,5-dimethylhydantoin could be present in admixture with (1), (2), or (3).

An even more preferred system for use in the practice of these embodiments of this invention is a bromine-based microbiocidal solution of a 1,3-dibromo-5,5-dialkylhydantoin in which one of the alkyl groups is a methyl group and the other alkyl group contains in the range of 1 to about 4 carbon atoms. Thus these preferred biocides comprise 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methythydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred member of this group of microbiocides is 1,3-dibromo-5,5-dimethylhydantoin. This compound is available in the marketplace in tablet or granular form under the trade designations Albrom® 100T biocide and Albrom® 100PC biocide (Albemarle Corporation).

When a mixture of two or more of the foregoing 1,3-dibromo-5,5-dialkylhydantoin biocides is used pursuant to this invention, the individual biocides of the mixture can be in any proportions relative to each other.

Methods for producing 1,3-dibromo-5,5-dialkylhydantoins are known and reported in the literature.

If desired, the 1,3-dihalo-5,5-dialkylhydantoins can be dissolved in a suitable innocuous, harmless, water-soluble organic solvent with or without water to form a solution which can be applied to surfaces of equipment, instruments, or apparatus. Depending upon the solvent used, the surfaces can then be further washed with clean water to remove residues from such solvent. Besides increasing the amount of 1,3-dihalo-5,5-dialkylhydantoin that can be put into solution thus facilitating formation of a concentrated solution, e.g., on the premises of the poultry processing, such a concentrated solution when diluted such as by addition to process water being used on the premises possesses microbiocidal activity from the 1,3-dihalo-5,5-dialkylhydantoin. Thus aqueous solutions used pursuant to this invention can contain suitably small amounts of an innocuous, harmless, water-soluble organic solvent, which non-toxic, at least at the dosage levels involved, such as acetonitrile.

In cases where extremely powerful biocidal activity is desired such as during periodic cleaning and disinfection operations, concentrated aqueous solutions of the microbiocides of this invention can be directly applied to surfaces of poultry processing equipment, instruments and/or apparatus infested with pathogenic microorganisms. Such concentrated solutions can contain, for example, as much as 150,000 ppm or 160,000 ppm or more of active bromine, and as much as about 66,667 ppm or about 71,111 ppm of active chlorine, as determinable by conventional starch-iodine titration. If desired, a portion of such concentrated solution can be diluted with any suitable amount of water before application directly to the surfaces of such poultry processing equipment, instruments and/or apparatus, provided of course that the diluted solution still contains a microbiocidally-effective amount of active bromine species for the use at hand. Also, concentrated solutions of this invention can be added to and thus used in diluted form in process water being used in poultry processing operations, such as for example, in water flowing through conduits, in water flowing into or being maintained in tanks, and in water being used in spraying equipment.

The amount (concentration) of the selected microbiocide utilized in the practice of this invention will vary depending on various factors such as the particular microbiocide being used, the nature and frequency of prior microbiocidal treatments, the types and nature of the microorganisms present, the amount and types of nutrients available to the microorganisms, the nature and extent of cleansing actions, if any, taken in conjunction with the microbiocidal treatment, the surface or locus of the microorganisms being treated, and so on. In any event, a microbiocidally-effective amount of the diluted aqueous solution of the microbiocide of this invention will be applied to or contacted with the microorganisms. Typically the diluted solution will contain a microbiocidally-effective amount of active halogen in the range of about 2 to about 1000 ppm (wt/wt), preferably in the range of about 2 to about 500 ppm (wt/wt), and more preferably in the range of about 25 to about 250 ppm (wt/wt), active halogen being determinable by use of the conventional DPD test procedure. If the actual active halogen in the solution consists of active chlorine, the concentration of the diluted solution used is preferably at least two to three times higher than the minimums of the foregoing ranges. In the case of the 1,3-dibromo-5,5-dialkylhydantoins used pursuant to this invention, a particularly preferred range for use in ordinary situations (e.g., washing hard surfaces such as tables, walls, floors, conveyor machinery or parts thereof such as converor belts or shackles, and knives or cutting blades) is in the range of about 50 to about 150 ppm (wt/wt) of active bromine. When contacting poultry carcasses or edible parts thereof with aqueous solutions formed from at least one 1,3-dibromo-5,5-dialkylhydantoin used pursuant to this invention, it is especially preferred to use in the water for washing or otherwise contacting the poultry carcasses or edible parts thereof, a microbiocidally effective amount of active bromine that does not significantly or appreciably bleach the skin of the caracass or have a significant or appreciable adverse effect upon the organleptic taste of cooked meat from the poultry such as the breast meat and thigh meat. Such amount is typically within the range of about 0.5 to about 30 ppm (wt/wt) and preferably in the range of about 5 to about 25 ppm (wt/wt) of active bromine as determinable by the DPD test procedure. Similar ranges are deemed applicable if using sulfamate-stabilized bromine chloride in these carcass washing operations. It will be understood that departures from the foregoing ranges can be made whenever deemed necessary or desirable, and such departures are within the spirit and scope of this invention.

Consequently, depending upon the way in which the microbiocide of this invention is being used, a microbiocidally-effective amount of the microbiocides of this invention can extend from as little as about 2 ppm up to as high as the maximum water solubility of the particular active halogen microbiocidal agent being used, at the temperature at which such active halogen microbiocidal agent is being used.

As can be seen from the above, there are two different types of procedures that are used for determining active halogen content, whether active chlorine, active bromine or both. For measuring concentrations in the vicinity of above about, say, 500 ppm or so (wt/wt) of active bromine or, say, above about 1100 ppm of active chlorine, starch-iodine titration is the preferred procedure. On the other hand, where concentrations are below levels in these vicinities, the conventional DPD test procedure is more suitable, as this test is designed for measuring very low active halogen concentrations, e.g., active chlorine concentrations in the range of from zero to about 11–12 ppm (wt/wt) or active bromine concentrations in the range of from zero to about 5 ppm (wt/wt). In fact, where the actual concentration of active chlorine is between, say, about 11–12 ppm and about 1100 ppm (wt/wt), or the where the actual concentration of active bromine is between, say, about 5 ppm and about 100 ppm (wt/wt), the test sample is typically diluted with pure water to reduce the actual concentration to be in the range of about 4 to about 11–12 ppm in the case of active chlorine and to be in the range of about 2 to about 5 ppm in the case of active bromine before making the DPD analysis. It can be seen therefore that while there is no critical hard-and-fast concentration dividing line between which procedure to use, the approximate values given above represent a practical approximate dividing line, since the amounts of water dilution of more concentrated solutions when using the DPD test procedure increase with increasing initial active halogen concentration, and such large dilutions can readily be avoided by use of starch-iodine titration when analyzing the more concentrated solutions. In short, with suitably dilute solutions use of the DPD test procedure is recommended, and with more concentrated solutions use of starch-iodine titration is recommended.

The starch-iodine titration procedure for determination of active halogen has long been known. For example, chapter XIV of Willard-Furman, *Elementary Quantitative Analysis*, Third Edition, D. Van Nostrand Company, Inc., New York, Copyright 1933, 1935, 1940 provides a description of starch-iodine titration. While details of standard quantitative analytical procedures for determination of active halogen in such product solutions by starch-iodine titration may vary from case to case, the results are normally sufficiently uniform from one standard procedure to another as not to raise any question of unreliability of the results. A recommended starch-iodine titration procedure is as follows: A magnetic stirrer and 50 milliliters of glacial acetic acid are placed in an iodine flask. The sample (usually about 0.2–0.5 g) for which the active halogen is to be determined is weighed and added to the flask containing the acetic acid. Water (50 milliliters) and aqueous potassium iodide (15%, wt/wt; 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active halogen is calculated using the weight of the sample and the volume of sodium thiosulfate solution titrated. In this way, the amount of active halogen such as active chlorine or active bromine in an aqueous product solution, regardless of actual chemical form, can be quantitatively determined.

The standard DPD test for determination of low levels of active halogen is based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozorie", J. Inst. Water Eng., 1974, 28, 139. While there are various modernized versions of the Palin procedures, the recommended version of the test is fully described in *Hach Water Analysis Handbook,* 3rd edition, copyright 1997. The procedure for "total chlorine" (i.e., active chlorine) is identified in that publication as Method 8167 appearing on page 379, Briefly, the "total chlorine" test involves introducing to the dilute water sample containing active halogen, a powder comprising DPD indicator powder, (i.e., N,N'-diethyldiphenylenediamine), KI, and a buffer. The active halogen species present react(s) with KI to yield iodine species which turn the DPD indicator to red/pink. The intensity of the coloration depends upon the concentration of "total chlorine" species (i.e., active chlorine") present in the sample. This intensity is measured by a calorimeter calibrated to transform the intensity reading into a "total chlorine" value in terms of mg/L $Cl_2$. If the active halogen present is active bromine, the result in terms of mg/L $Cl_2$ is multiplied by 2.25 to express the result in terms of mg/L $Br_2$ of active bromine.

In greater detail, the DPD test procedure is as follows:

1. To determine the amount of species present in the water which respond to the "total chlorine" test, the water sample should be analyzed within a few minutes of being taken, and preferably immediately upon being taken.

2. Hach Method 8167 for testing the amount of species present in the water sample which respond to the "total chlorine" test involves use of the Hach Model DR 2010 colorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.

In the practice of this invention the microbiocidal system can be used in various ways. For example, a microbiocidally effective amount of a microbiocide of this invention, preferably a bromine-based microbiocidal system, is applied to the locus of the microorganisms to be eradicated or controlled so that the microbiocidal system comes in contact with these microorganisms. The application can be made by thorough application by pouring, spraying, wet mopping, flooding, and/or wet wiping infested or potentially infested surfaces or areas of the processing equipment and environs such as flooring, walls, tables, conveyors, stanchions, conduits, tanks, and drains with a biocidally-effective amount of an aqueous solution the microbiocide. Where applicable and possible, portions of the processing apparatus can be immersed in an aqueous solution of the microbiocide, with temporary disassembly, if necessary. Such applications should be conducted routinely on a frequency sufficient to ensure that exposure of the poultry being processed to dangerous microorganisms, such as bacteria and biofilms is prevented to the greatest extent possible. For best results these operations should be conducted in conjunction or association with thorough cleaning operations such as scrubbing, scouring, scraping and, otherwise removing infestations of biofouling or biofilms, whether visible or invisible. After contacting the microorganisms with the microbiocide for a suitable period of time to ensure penetration into polysaccharide slimes and other defense mechanisms of various species of these microorganisms, the entire disinfected area should be washed, e.g., hosed down, with clean water and preferably the washings themselves should be disinfected with additional microbiocide of this invention, preferably a bromine-based microbiocide, before discharge. The contact times will of course vary depending upon the frequency and thoroughness of the cleaning and disinfection operations and the identity and concentration of the particular microbiocidal solution being employed. Generally speaking contact times may fall in the range of from about a few minutes to a few hours, but any period of time that effects the eradication or control of the microbial population in the poultry processing areas should be used and is within the scope of this invention.

Another mode of applying the microbiocidally-effective amounts of solid-state microbiocides of these embodiments of the invention is to cause the microbiocide to be leached into water streams passing through conduits and into tanks or other washing devices utilized in the processing of the poultry. For example, suitable solid forms of the microbiocide, preferably a bromine-based microbiocide, such as tablets, briquettes, pellets, nuggets, or granules are placed in suitable feeding devices through which a stream of water is passed. The passage of the water through the bed of the microbiocide results in the stream continuously dissolving small quantities of the microbiocide to thereby provide microbiocidally effective amounts of the microbiocide in the water. 1,3-Dibromo-5,5-dimethylhydantoin is especially preferred for use in this mode of application because of its relatively low solubility and thus relatively slow rate of dissolution in water at ambient room temperatures. This translates into relatively long periods of use before need of refilling the device holding the solids. By way of example, the solubility of 1,3-dibromo-5,5-dimethylhydantoin in water at 75° F. (ca. 24° C.) is 405 ppm expressed as $Cl_2$ whereas the solubilities of N,N'-bromochloro-5,5-dimethylhydantoin and of the commercial mixture of N,N'-bromochloro-5,5-dimethylhydantoin and 1,3-dichloro-5-ethyl-5-methylhydantoin at the same temperature are, respectively, 890 ppm and 1905 ppm, both expressed as $Cl_2$.

An especially cost-effective, operationally efficient, and highly preferred way of forming aqueous microbiocidal solutions of one or more 1,3-dibromo-5,5-dialkylhydantoins in which one of the alkyl groups is a methyl group and the other alkyl group contains in the range of 1 to about 4 carbon atoms, most preferably 1,3-dibromo-5,5-dimethylhydantoin, ("dibromodialkylhydantoin(s)") comprises passing water through a bed of one or more such dibromodialkylhydantoin (s) in granular, nugget, pellet, tablet or other non-powdery particulate form ("bed") disposed in a canister, tank, or other similar vessel ("tank"). Preferably the tank has a pressure sealable port at its upper portion for periodically replenishing the contents of the bed, and the water is caused to flow upwardly through a portion of the bed. More preferably, the tank is elongated in an upward direction so that the bed is longer from top to bottom than from side to side, this upward water flow is dispensed into the bed to flow upwardly through only a lower portion of the bed, and thence substantially horizontally through a port disposed between the lower and the upper portions of the bed and tank. In this way the upper portion of the bed serves as a reserve supply of contents of the bed which automatically feeds into the lower portion of the bed under gravity a as the lower portion of the bed is slowly but substantially uniformly dissolved away in the water flow. Thus in this operation the water flow is preferably at least a substantially continuous flow, and most preferably, is a continuous flow. Methods for producing granules, tablets or other non-powdery particulate forms of 1,3-dibromo-5,5-dimethylhydantoin are described in detail in commonly-owned copending applications PCT/US 01/01541, 01/01545, and 01/01585, all filed Jan. 17, 2001, each claiming priority based on respective earlier-filed corresponding U.S. applications. Excellent process technology for producing 1,3-dibromo-5,5-dimethylhydantoin for use in making such granules, tablets or other non-powdery particulate forms is described in detail in commonly-owned copending application PCT/US 01/01544, filed Jan. 17, 2001, claiming priority based on an earlier-filed corresponding U.S. application. The disclosures of each such PCT and U.S. application is incorporated herein by reference. Particularly preferred apparatus for use in conjunction with such granules, tablets or other non-powdery particulate forms of these dibromodialkylhydantoin(s) in forming aqueous microbiocidal solutions thereof is available from Neptune Chemical Pump Company, a division of R.A. Industries, Inc., Lansdale, Pa. 19446, as "Bromine Feeders" Models BT-15, BT-40, BT42, BT-80, BT-160, BT-270, and BT-350, or equivalent. Excellent results are achieved using combinations of Model BT-40 with granules of 1,3-dibromo-5,5-dimethylhydantoin Albrom® 100 biocide available from Albemarle Corporation. Single charges of such microbiocides in tablet or granular form in such device can provide continuous highly-effective microbiocidal activity in bodies of end use water at ordinary outdoor temperatures for as long as five (5) months without need for replenishment.

In the case of the more water-soluble microbiocides used pursuant to this invention, another suitable method of effecting contact between the microbiocide and the microorganisms is to pump an aqueous solution containing a microbiocidally-effective amount of the microbiocide through the conduits and into the tanks or other washing devices, such as scalding tanks and chill tanks, utilized in the processing of the poultry. Variants of this procedure include dispensing portion-wise as by gravity dripping an aqueous solution of the microbiocide directly into a tank or other vessel in which poultry are to be or are being processed.

A further mode of application pursuant to these embodiments of the invention involves applying to or contacting the poultry itself, typically promptly before and/or after slaughter, with an aqueous solution of the microbiocide. After providing a suitable contact time to eradicate bacteria on the surfaces of the poultry, the poultry can then be washed down to remove both the excess microbiocide and the dispatched microbial population from the exposed surfaces of the fowl itself. The internal organs of the fowl after slaughter can also be treated and washed down in the same manner. The application(s) of the microbiocidal solution(s) in this manner can take any suitable form, e.g., use of aqueous sprays containing a microbiocidally-effective amount of the microbiocide being used, or immersion of the fowl or internal organs thereof in one or more tanks containing aqueous solutions of microbiocidally-effective amounts of the microbiocide being used.

Preferably two or more of the foregoing methods of application of the microbiocides of this invention are used. Thus in a preferred embodiment a microbiocide of these embodiments of the invention, preferably an aqueous bromine-based microbiocidal solution, is applied by (i) periodically contacting at least portions, if not all, of the poultry processing apparatus to disinfection or sanitization with a microbiocidally-effective amount of an aqueous solution of at least one microbiocide of these embodiments of the invention, preferably a bromine-based microbiocide, and (ii) contacting the exposed surfaces of the poultry with a microbiocidally-effective amount of an aqueous solution of at least one microbiocide of these embodiments of the invention, preferably a solution of abromine-based microbiocide, before and/or after, preferably after, dispatching the fowl. In another preferred embodiment, a microbiocide of these embodiments of the invention, preferably an aqueous bromine-based microbiocidal solution, is applied by (i) periodically contacting at least portions, if not all, of the poultry processing apparatus to disinfection or sanitization with a microbiocidally-effective amount of an aqueous solution of at least one microbiocide of these embodiments of the invention, preferably a bromine-based microbiocide, and (ii) contacting the edible portions and/or internal organs of the dispatched fowl with a microbiocidally-effective amount of an aqueous solution of at least one microbiocide of these embodiments of the invention, preferably a solution of a bromine-based microbiocide.

Particularly preferred processes of this invention are those wherein the fowl are processed by a series of steps which comprise the following: (a) suspending the fowl in moving clamps or shackles, (b) stunning, but not killing, the fowl such as by use of a suitable gas, or by contacting at least the heads of the fowl with a water-applied electric shock to stun the fowl, e.g., by immersing the heads in a water bath carrying a suitable current to effect the stunning, (c) cutting the jugular veins and/or carotid arteries at the neck of the stunned fowl either manually with a knife or automatically with a mechanical cutting device, (d) draining blood from the carcasses, (e) scalding the birds with hot water, e.g., in a scalding tank, to facilitate feather removal, (f) defeathering the fowl, (g) removing the heads and feet from the fowl, (h) eviscerating the fowl either manually with a knife, or automatically with mechanical evisceration apparatus, (i) separating the viscera from the carcasses, (j) washing the carcasses, and (k) chilling the carcasses, e.g., in water such as by passage of the carcasses through at least one and often two chill tanks, or by air chilling. The scalding step will typically be conducted at water temperatures in the range of about 50 to about 60° C., with the lower temperatures being preferred for retention of normal yellow-colored skin. The higher temperatures will more usually be used in connection with turkeys and spent egg-layer hens. The chilling temperatures used will typically reduce the carcass temperature to below about 40° C., with final temperatures of the finished carcasses for shipment being as low as about −2° C. Other steps can be included and in some cases one or more of the steps (a) through (j) may be altered or revised or the sequence of the steps may to some extent be altered or revised, to adapt to given circumstances. Examples of extra steps that may be included are inspection steps, e.g., by governmental regulatory personnel, and wax-dipping in the case of water fowl to enhance the extent of defeathering. Inspections are often conducted subsequent to the evisceration step, such as before separating the viscera from the carcasses. Wax dipping will typically be used when processing waterfowl, the feathers of which typically are more difficult to remove than, say, chickens. Wax dipping will typically be performed directly after use of feather-picking machines which utilize rubber "fingers" to beat off the feathers. The wax dipping step will typically involve dipping the partially defeathered carcass into a molten wax contained in a tank, allowing the wax to harden on the carcass, and then removing the wax coating as by peeling it off along with feathers embedded in the wax. This operation can be repeated as desired, before proceeding to the next step in the process, e.g., removal of the heads and feet. One illustrative example of a suitable revision of the sequence of steps, would be to conduct step (g) before step (d) instead of after step (f). Upon a reading of this disclosure, other suitable sequence revisions may well become obvious to one of ordinary skill in the art, and thus need not be further elaborated upon here.

In the above processing, the microbiocidal action of the microbiocides of these embodiments of the invention, preferably one or more applicable bromine-based microbiocides used pursuant to this invention, can be applied at any of a variety of suitable stages in the operation. For example, an applicable microbiocidal solution of this invention can be applied to any or all of the processing equipment used including knives, conveying apparatus, the surfaces of emptied scaling tanks, defeathering apparatus, (e.g., rubber "fingers" etc.), knives and mechanical apparatus used for cutting or eviscerating the fowl, all surfaces that come in contact with the blood or the viscera of the fowl, including tables, conveyor belts, etc., and all surfaces that come in contact with the carcasses after separation of the viscera therefrom. The applicable sanitizing solutions of this invention can be applied to by immersion, spraying, flooding, or any other way ofensuring that the microbiocidally-effective solution contacts the surfaces that contain or are exposed to the undesirable microorganisms such as bacteria and/or biofilm (biofouling).

Another way by which, in the above processing the microbiocidal action of the applicable microbiocides of this invention, preferably one or more applicable bromine-based microbiocides used pursuant to this invention, can be applied involves including a microbiocidally-effective amount of the microbiocide to the water being used at one or more stages of the processing. Thus the water in the scalding tank(s) and/or in the chill tank(s) can be so treated. Another mode is to include a microbiocidally-effective amount of the microbiocide to the water used in washing the carcasses and the viscera at various points where these parts are handled, separated, and/or processed. The dosage levels at these different points in the processing can be the same or different as deemed necessary or desirable.

The practice and advantages of this invention are illustrated by the following non-limiting Examples.

Example 1

Comparative tests were conducted to determine the effect on poultry carcass bacteria (*Escherichia coli* field strain) during a normal 1.5-hour chill tank immersion in water containing different microbiocidal compositions. The effect of these treatments on the residual chill tank water was also investigated. Carcasses were first immersed in a warm bath containing $10^4$ *E coli* per mL of liquid. Carcasses were then immersed in chill tanks containing normal organic fluids (blood, fat, skin, and meat particles) and containing one of the respective microbiocidal compositions under test. Total bacteria count of whole bird (both inside and outside) was used to determine efficacy of various microbiocidal compositions. The microbiocidal compositions tested were Aquatize® biocide (Bioxy Incorporated, 3733 National Drive, Suite 115, Raleigh, N.C. 27612-4845), sodium hypochlorite (Clorox® bleach), sodium bromide (supplied as a 40% solution in water), combinations of sodium hypochlorite and sodium bromide, and a concentrated alkaline aqueous solution produced from bromine chloride and sulfamate anion (SSBC) (Stabrom® 909 biocide; Albemarle Corporation).

The trial events and experimental design used were as follows:
a) For all treatments a total of 190 birds were processed in a normal fashion. Each treatment involved use of 10 birds.
b) A warm (100° F.) bath was prepared containing $5 \times 10^4$ DelMarVa (Delaware-Maryland farm area) field *Escherichia coli* stain bacteria per mL. At least 200 mL of total bath fluid was provided for each bird.
c) All birds (both controls and treated) were randomly immersed into the warm bath. Both the inside and outside carcass areas were immersed to assure complete coverage.
d) Each separate chill tank water solution (normal tap water adjusted pH to 8.5, ice added to produce temperatures of <45° F.) contained $2 \times 10^3$ per mL bacteria.
e) The chill tank water solutions (at least 750 mL each) were be prepared for each disinfecting treatment, and birds were immersed for a period of 1.5 hours.
f) Each 10 minutes during the 1.5 hour chilling period, the birds were completely lifted out of solution and then reimersed in the solution. After the 1.5 hour chilling period, the birds were taken from the chill water and drained for 30 seconds, then promptly (within 5 minutes) placed into a sterile whole bird stomacher bag containing 400 mL diluent (Butterfield's Phosphate Diluent) bacteria collection.
g) Diluent (400 mL) was added to each carcass contained in a sterile stomacher bag while making sure to pour the diluent into the inside of the abdominal cavity. The carcass was rinsed inside and out with a rocking motion for one minute (ca. 35 RPM). This was best done by grasping the broiler carcass with one hand and the closed top of the bag with the other then rocking with a reciprocal motion in a 18–24 inch arc, assuring that all carcass surfaces (interior and exterior) were rinsed.
h) The rinse solutions were then transferred from each stomacher bag into individual sample bottles, taking care to ensure that the information on the date of collection, time of collection, and treatment group matched that of the sample. Each bottle was sealed with parafilm and stored in a refrigerator.
i) Dilution of the fluids was conducted such that a 25–250 count was present on the MacConkey plate. After the fluids had been diluted, 0.1 mL of fluid was be placed on a MacConkey agar plate and bacteria counts determined. In cases where the goal of a 25–250 count on the plate was not achieved, another dilution and replating were conducted.
j) After all carcasses for each treatment had been dipped, water sample bacteria were determined.
k) Total bacteria per bird were calculated.

The chill water used was composed per liter of 950 mL of tap water, 50 mL of blood, 10 g of ground abdominal fat, and 10 g of meat particles. To form the bacteria culture used as the test bacteria source, an overnight culture in BHI broth was transferred to fresh BHI broth and incubated at 37° C. for 1.5 hour to a population density of approximately $8 \times 10^6$ DFU per mL (optical density at 600 nm, –0.1). This bacteria solution was added equally at $5 \times 10^4$ to provide a water solution to predip all birds prior to chilling. In addition, prior to dipping the birds for the 1.5-hour chill period, additional bacteria were added to the chill water in the amount of $2 \times 10^3$ total bacteria per mL of chill water. Poultry carcass microbial contamination measurement was achieved by the complete washing of the entire carcass surface (inside and outside) using suitable sterile stripping solution followed by collection and plating of the stripping solution for bacterial enumeration.

Table 1 presents the experimental design of this group of tests.

TABLE 1

| Test Group | Test Material & Disinfectant Level |
|---|---|
| 1 | No disinfectant[1] |
| 2 | Aquatize ® biocide (dilution 1:700), contains 50 ppm sodium chlorite |
| 3 | Aquatize ® biocide (dilution 1:350), contains 100 ppm sodium chlorite |
| 4 | Aquatize ® biocide (dilution 1:250), contains 150 ppm sodium chlorite |
| 5 | Clorox ® bleach 12.5% Cl (dilution 1:2,500), Contains 50 ppm $Cl_2$ equivalent[2] |
| 6 | Clorox ® bleach 12.5% Cl (dilution 1:1,250), Contains 100 ppm $Cl_2$ equivalent |
| 7 | Clorox ® bleach 12.5% Cl (dilution 1:800), Contains 150 ppm $Cl_2$ equivalent |
| 8 | SSBC (dilution 1:12,500), Contains 50 ppm $Cl_2$ equivalent (1.57 times $Cl_2$) |
| 9 | SSBC (dilution 1:6,250), Contains 100 ppm $Cl_2$ equivalent (1.57 times $Cl_2$) |
| 10 | SSBC (dilution 1:4,000), Contains 150 ppm $Cl_2$ equivalent (1.57 times $Cl_2$) |
| 11 | Bleach and Sodium Bromide (1:1 mole ratio mix), bleach dilution 1:3,500 & 40% NaBr solution dilution 1:28,000, Contains 50 ppm $Cl_2$ equivalent (1:1 $Cl_2$ equivalent) |
| 12 | Bleach and Sodium Bromide (1:1 mole ratio mix), bleach dilution 1:1,750 & 40% NaBr solution dilution 1:14,000, Contains 100 ppm $Cl_2$ equivalent (1:1 $Cl_2$ equivalent) |
| 13 | Bleach and Sodium Bromide (1:1 mole ratio mix), bleach dilution 1:1,200 & 40% NaBr solution dilution 1:9,300, Contains 150 ppm $Cl_2$ equivalent (1:1 $Cl_2$ equivalent) |
| 14 | Bleach and Sodium Bromide (2:1 mole ratio mix), bleach dilution 1:3,000 & 40% NaBr solution dilution 1:50,000, Contains 50 ppm $Cl_2$ equivalent (1:1 $Cl_2$ equivalent) |
| 15 | Bleach and Sodium Bromide (2:1 mole ratio mix), bleach dilution 1:1,500 & 40% NaBr solution dilution 1:25,000, Contains 100 ppm $Cl_2$ equivalent (1:1 $Cl_2$ equivalent) |
| 16 | Bleach and Sodium Bromide (2:1 mole ratio mix), bleach dilution 1:1,000 & 40% NaBr solution dilution 1:16,600, Contains 150 ppm $Cl_2$ equivalent (1:1 $Cl_2$ equivalent) |
| 17 | Sodium Bromide (40% solution), Dilution 1:8,000, Contains 50 ppm $Cl_2$ equivalent (1:1 $Cl_2$ equivalent) |
| 18 | Sodium Bromide (40% Solution), Dilution 1:4,000, Contains 100 ppm $Cl_2$ equivalent (1:1 $Cl_2$ equivalent) |
| 19 | Sodium Bromide (40% solution), Dilution 1:2,670, Contains 150 ppm $Cl_2$ equivalent (1:1 $Cl_2$ equivalent) |

[1] Negative Control contained contaminated (bacteria $2.67 \times 10^5$ per mL) water.
[2] Positive Control is normal poultry industry practice of adding 50 ppm $Cl_2$ equivalent.

Tables 2–4 show, respectively, the method of determining the dilution levels for achieving 50 ppm, 100 ppm, and 150 ppm $Cl_2$ equivalents in the case of the chill tank solutions formed from Clorox® bleach solution and a 40% water solution of sodium bromide.

TABLE 2

Dilutions for 50 ppm $Cl_2$ Equivalent

| Molarity Ratio | Percentage (% of each ingredient) | | Amount per liter 50 ppm (ppm of each) | | Amount per liter 50 ppm (ul/liter) | |
|---|---|---|---|---|---|---|
| | Bleach | NaBr 40 | Bleach | NaBr 40 | Bleach | NaBr 40 |
| 1:1 | 72 | 28 | 36 | 14 | 288 | 35 |
| 2:1 | 84 | 16 | 42 | 8 | 336 | 20 |

TABLE 3

Dilutions for 100 ppm $Cl_2$ Equivalent

| Molarity Ratio | Percentage (% of each ingredient) | | Amount per liter 100 ppm (ppm of each) | | Amount per liter 100 ppm (ul/liter) | |
|---|---|---|---|---|---|---|
| | Bleach | NaBr 40 | Bleach | NaBr 40 | Bleach | NaBr 40 |
| 1:1 | 72 | 28 | 72 | 28 | 576 | 70 |
| 2:1 | 84 | 16 | 84 | 16 | 672 | 40 |

TABLE 4

Dilutions for 150 ppm $Cl_2$ Equivalent

| Molarity Ratio | Percentage (% of each ingredient) | | Amount per liter 150 ppm (ppm of each) | | Amount per liter 150 ppm (ul/liter) | |
|---|---|---|---|---|---|---|
| | Bleach | NaBr 40 | Bleach | NaBr 40 | Bleach | NaBr 40 |
| 1:1 | 72 | 28 | 108 | 42 | 864 | 105 |
| 2:1 | 84 | 16 | 126 | 24 | 1008 | 60 |

NaBr = SANTBROM 40 Biocide (contains 40% sodium bromide, water solution).
Clorox ® bleach (Bleach) contains 12.5% chlorine.

Calculations for dilutions using the other biocides of this group that were tested were based on the following: Aquatize® biocide is a solution containing 3.67% sodium chlorite, and Stabrom® 909 biocide solution, it was calculated as 1.57 times $Cl_2$ equivalent level. The results of this group of tests are summarized in Tables 5–7.

TABLE 5

Carcass Bacteria Reduction

| Test Group | Test Material Disinfectant Level | Mean Bacteria Reduction[1] |
|---|---|---|
| 1 | Negative Control | No reduction |
| 2 | Aquatize ® biocide (dilution 1:700) | $4.25 \times 10^2$ |
| 3 | Aquatize ® biocide (dilution 1:350) | $3.06 \times 10^3$ |
| 4 | Aquatize ® biocide (dilution 1:250) | $6.67 \times 10^3$ |
| 5 | Clorox ® bleach, 12.5% $Cl_2$ (dilution 1;2,500) | $1.03 \times 10^2$ |
| 6 | Clorox ® bleach, 12.5% $Cl_2$ (dilution 1:1,250) | $5.11 \times 10^2$ |
| 7 | Clorox ® bleach, 12.5% $Cl_2$ (dilution 1:800) | $9.89 \times 10^2$ |
| 8 | SSBC (dilution 1:12,500) | $2.41 \times 10^2$ |
| 9 | SSBC (dilution 1:6,250) | $5.87 \times 10^3$ |
| 10 | SSBC (dilution 1:4,000) | $4.69 \times 10^4$ |
| 11 | Bleach and sodium bromide (1:1 mole ratio mix) Bleach 1:3,500 & NaBr dilution 1:28,000) | $3.52 \times 10^4$ |
| 12 | Bleach and sodium bromide (1:1 mole ratio mix) Bleach 1:1,750 & NaBr dilution 1:14,000) | $8.87 \times 10^4$ |
| 13 | Bleach and sodium bromide (1:1 mole ratio mix) Bleach 1:1,200 & NaBr dilution 1:9,300) | $2.27 \times 10^5$ |
| 14 | Bleach and sodium bromide (2:1 mole ratio mix) Bleach 1:3,000 & NaBr dilution 1:50,000) | $1.09 \times 10^3$ |
| 15 | Bleach and sodium bromide (2:1 mole ratio mix) Bleach 1:1,500 & NaBr dilution 1:25,000) | $1.55 \times 10^4$ |
| 16 | Bleach and sodium bromide (2:1 mole ratio mix) Bleach 1:1,000 & NaBr dilution 1:16,600) | $5.21 \times 10^4$ |
| 17 | Sodium bromide, 40% solution, Dilution 1:8,000 | 92 |
| 18 | Sodium bromide, 40% solution, Dilution 1:4,000 | $6.54 \times 10^2$ |
| 19 | Sodium bromide, 40% solution, Dilution 1:2,670 | $1.73 \times 10^3$ |

[1] The value represents an average of 10 birds per treatment.
[2] Test group 1 carcass contained $2.67 \times 10^5$ total bacteria count.

TABLE 6

Carcass Bacteria Reduction Results (% reduction)

| Test Group | Mean Bacteria Reduction[1] | Mean Bacteria Reduction Count[1] | Percent Bacteria Reduction From Control[1] |
|---|---|---|---|
| 1 | No reduction[2] [2)] | 267,000 | Control |
| 2 | $4.25 \times 10^2$ | 425 | 0.159% |
| 3 | $3.06 \times 10^3$ | 3,060 | 1.146% |
| 4 | $6.67 \times 10^3$ | 6,670 | 2.498% |
| 5 | $1.03 \times 10^2$ | 103 | 0.039% |
| 6 | $5.11 \times 10^2$ | 511 | 0.191% |
| 7 | $9.89 \times 10^2$ | 989 | 0.370% |
| 8 | $2.41 \times 10^2$ | 241 | 0.090% |
| 9 | $5.87 \times 10^3$ | 5,870 | 2.199% |
| 10 | $4.69 \times 10^4$ | 46,900 | 17.566% |
| 11 | $3.52 \times 10^4$ | 35,200 | 13.184% |
| 12 | $8.87 \times 10^4$ | 88,700 | 33.221% |
| 13 | $2.27 \times 10^5$ | 227,000 | 85.019% |
| 14 | $1.09 \times 10^3$ | 1,090 | 0.408% |
| 15 | $1.55 \times 10^4$ | 15,500 | 5.805% |
| 16 | $5.21 \times 10^4$ | 52,100 | 19.513% |
| 17 | 92 | 92 | 0.034% |
| 18 | $6.54 \times 10^2$ | 654 | 0.245% |
| 19 | $1.73 \times 10^3$ | 1,730 | 0.648% |

[1]The value represents an average of 10 birds per treatment.
[2]Test group 1 carcass contains $2.67 \times 10^5$ total bacteria count.

TABLE 7

Chill Water Bacteria Count

| Test Group | Test Material Disinfectant Level | Mean Bacteria Reduction[1] |
|---|---|---|
| 1 | Negative Control | $5.11 \times 10^3$ |
| 2 | Aquatize ® biocide (dilution 1:700) | $2.43 \times 10^3$ |
| 3 | Aquatize ® biocide (dilution 1:350) | $8.54 \times 10^2$ |
| 4 | Aquatize ® biocide (dilution 1:250) | $2.21 \times 10^2$ |
| 5 | Clorox ® bleach, 12.5% $Cl_2$ (dilution 1:2,500) | $5.43 \times 10^3$ |
| 6 | Clorox ® bleach, 12.5% $Cl_2$ (dilution 1:1,250) | $4.24 \times 10^3$ |
| 7 | Clorox ® bleach, 12.5% $Cl_2$ (dilution 1:800) | $1.05 \times 10^3$ |
| 8 | SSBC (dilution 1:12,500) | $4.83 \times 10^3$ |
| 9 | SSBC (dilution 1:6,250) | $1.64 \times 10^3$ |
| 10 | SSBC (dilution 1:4,000) | $3.02 \times 10^2$ |
| 11 | Bleach and sodium bromide (1:1 mole ratio mix) Bleach 1:3,500 & NaBr dilution 1:28,000 | $2.55 \times 10^2$ |
| 12 | Bleach and sodium bromide (1:1 mole ratio mix) Bleach 1:1,750 & NaBr dilution 1:14,000 | $1.36 \times 10^2$ |
| 13 | Bleach and sodium bromide (1:1 mole ratio mix) Bleach 1:1,200 & NaBr dilution 1:9,300 | 43 |
| 14 | Bleach and sodium bromide (2:1 mole ratio mix) Bleach 1:3,000 & NaBr dilution 1:50,000 | $1.98 \times 10^3$ |
| 15 | Bleach and sodium bromide (2:1 mole ratio mix) Bleach 1:1,500 & NaBr dilution 1:25,000 | $6.46 \times 10^2$ |
| 16 | Bleach and sodium bromide (2:1 mole ratio mix) Bleach 1:1,000 & NaBr dilution 1:16,600 | $3.47 \times 10^2$ |
| 17 | Sodium bromide (40% solution), Dilution 1:8,000 | $4.67 \times 10^3$ |
| 18 | Sodium bromide (40% solution), Dilution 1:4,000 | $3.49 \times 10^3$ |
| 19 | Sodium bromide (40% solution), Dilution 1:2,670 | $2.23 \times 10^3$ |

[1]The value represents bacteria count per mL of treatment water.

Example 2

The procedure of Example 1 was repeated except that the materials tested for microbiocidal activity were (a) sodium hypochlorite (Clorox® bleach), (b) the combination of sodium bromide and sodium hypochlorite, and (c) 1,3-dibromo-5,5-dimethylhydantoin (DBDMH), 100 birds were used in this group of tests, and the chill water was composed per liter of 950 mL of water, 50 mL of blood, 10 g of ground abdominal fat, 10 g of meat particles, and 10 g of skin with fat.

The experimental design used in this group of tests is summarized in Table 8.

TABLE 8

| Test Group | Active Ingredient or equivalent | Test Material Disinfectant Level |
|---|---|---|
| 1 | None | No disinfectant |
| 2 | Chlorine (50 ppm) | Clorox ® bleach 12.5% $Cl_2$ (dilution 1:2,500), Contains 50 ppm chlorine[2] |
| 3 | Chlorine (100 ppm) | Clorox ® bleach 12.5% $Cl_2$ (dilution 1:1,250) Contains 100 ppm chlorine |
| 4 | Chlorine (150 ppm) | Clorox ® bleach 12.5% $Cl_2$ (dilution 1:800) Contains 150 ppm chlorine |
| 5 | Chlorine (50 ppm total) | Bleach and Liquid Sodium Bromide (1:1 mole ratio mix) Bleach dilution 1:3,500 & NaBr dilution 1:28,000 Contains 50 ppm chlorine equivalent (1:1 $Cl_2$ equivalent) |
| 6 | Chlorine (100 ppm total) | Bleach and Liquid Sodium Bromide (1:1 mole ratio mix) Bleach dilution 1:1,750 & NaBr dilution 1:14,000 Contains 100 ppm chlorine equivalent (1:1 $Cl_2$ equivalent) |
| 7 | Chlorine (150 ppm total) | Bleach and Liquid Sodium Bromide (1:1 mole ratio mix) Bleach dilution 1:1,200 & NaBr dilution 1:9,300 Contains 150 ppm chlorine equivalent (1:1 $Cl_2$ equivalent) |
| 8 | Chlorine (50 ppm total) | DBDMH (equivalent to 50 ppm $Cl_2$ level)-0.9 g per liter Contains 50 ppm chlorine equivalent (1:1 $Cl_2$ equivalent) |
| 9 | Chlorine (100 ppm) | DBDMH (equivalent to 100 ppm $Cl_2$ level)-1.7 g per liter Contains 100 ppm chlorine equivalent (1:1 $Cl_2$ equivalent) |
| 10 | Chlorine (150 ppm) | DBDMH (equivalent to 150 ppm $Cl_2$ level)-3.4 g per liter Contains 150 ppm chlorine equivalent (1:1 $Cl_2$ equivalent) |

[1]Negative control contained contaminated (bacteria $2.67 \times 10^5$ per mL) water.
[2]Positive control is normal poultry industry practice of adding 50 ppm chlorine.

The microbiocidal solution of this invention was prepared in the following manner:

1. To form a stock solution, 100 g of 1,3-dibromo-5,5-dimethylhydantoin (DBDMH) was stirred into 10 liters (10,000 mL) of water for 20 minutes. After filtration, the resulting clear solution contains 1300 mg per liter as $Br_2$. This corresponds to 580 mg per liter (or 580 ppm $Cl_2$) when expressed as $Cl_2$.
2. The washing solution of DBDMH having a content of 50 ppm of $Cl_2$ equivalent solution was formed by mixing 875 mL of the above stock solution with 10 liters (10,000 mL) of the above prepared chicken chill water solution. The washing solutions of DBDMH containing 100 ppm $Cl_2$ equivalent and 150 ppm $Cl_2$ equivalent were prepared in the same manner except that 1750 mL and 2625 mL, respectively, of the above stock solution were mixed with separate 10-liter portions of the above prepared chicken chill water solution.

Table 9 summaries the results obtained in this group of tests.

TABLE 9

Carcass Bacteria Reduction

| Test Group | Test Material Disinfectant Level | Whole Bird Bacteria Reduction (%) | Mean Chill Water Bacteria Reduction (%)[1] |
|---|---|---|---|
| 1 | No disinfectant | Control[2] | Control |
| 2 | Clorox ® bleach[3], 50 ppm $Cl_2$ | 6.6% | 8.2% |
| 3 | Clorox ® bleach, 100 pp, $Cl_2$ | 28.2% | 32.8% |
| 4 | Clorox ® bleach 150 ppm $Cl_2$ | 41.1% | 59.3% |
| 5 | NaBr 50 ppm $Cl_2$ equivalent + Bleach | 14.8% | 18.4% |
| 6 | NaBr 100 ppm $Cl_2$ equivalent + Bleach | 38.5% | 41.6% |
| 7 | NaBr 150 ppm $Cl_2$ equivalent + Bleach | 73.5% | 84.7% |
| 8 | DBDMH, 50 ppm $Cl_2$ equivalent | 99.9999% | 99.9999% |
| 9 | DBDMH, 100 ppm $Cl_2$ equivalent | 99.9999% | 99.9999% |
| 10 | DBDMH, 150 ppm $Cl_2$ equivalent | 99.9999% | 99.9999% |

[1]The value represents bacteria count per mL of treatment water.
[2]Negative control contained contaminated (bacteria $2.67 \times 10^5$ per mL) water.
[3]Positive control is normal poultry industry practice of adding 50 ppm chlorine.

Example 3

This group of tests was conducted to determine the effect of Clorox® bleach, Aquatize® biocide, and 1,3-dibromo-5,5-dimethylhydantoin (DBDMH) on carcass bacteria (Escherichia coli field strain) residual after 1.5-hour in a chill tank "soup". Tests were conducted with soups at pH 7, pH 8 and pH 9 (adjusted by trisodium phosphate) for whole bird bacteria counts. Tests at pH 8 were conducted for individual bacteria counts.

In general the tests involved normal processing of 56-day-old birds and immersing the carcasses first in a warm bath containing $10^4$ per mL Escherichia coli, $10^4$ per mL Salmonella enteritidis, $10^4$ per mL Pseudomonas aeruginosa, $10^4$ per mL Campylobacter jejuni, and $10^4$ per mL spoilage bacteria each from three strains (Listena monocytogenes and Shigella sonnei). The carcasses were then immersed in a chill tank "soup", containing normal organic fluids (blood, fat, skin, and meat particles) and containing the microbiocides on the test.

Tables 10 and 11 summarize the experimental design of these group of test.

TABLE 10

Whole Bird Bacteria Counts at pH 7, pH 8, and pH 9

| Test Group | Test Material (Chill Tank) | Reps | Birds/Rep |
|---|---|---|---|
| 1 | None (Control) | 5 | 10 |
| 2 | Clorox ® Bleach (20 ppm $Cl_2$ equivalent) | 5 | 10 |
| 3 | Aquatize ® (1:500 dilution) | 5 | 10 |
| 4 | Aquatize ® (1:1000 dilution) | 5 | 10 |
| 5 | DBDMH (10 ppm $Cl_2$ equivalent) | 5 | 10 |
| 6 | DBDMH (20 ppm $Cl_2$ equivalent) | 5 | 10 |

TABLE 11

Individual Bird Bacteria Counts at pH 8

| Test Group | Test Material (Chill Tank) | Reps | Birds/Rep |
|---|---|---|---|
| 7 | None (Control) | 5 | 5 |
| 8 | Clorox ® Bleach (20 ppm $Cl_2$ equivalent) | 5 | 5 |
| 9 | DBDMH (10 ppm $Cl_2$ equivalent) | 5 | 5 |
| 10 | DBDMH (20 ppm $Cl_2$ equivalent) | 5 | 5 |

The bacteria stock solution used for this group of tests was prepared by growing each bacteria sample in the appropriate broth shown in Table 12. Each such broth had a volume of at least 500 mL and the bacteria were allowed to grow for at least 6 hours. The containers were observed and not allowed to develop a heavy, cloudy visual appearance which would indicate that the growth had developed for too long a period. Thus the solutions had the appearance of only being foggy or somewhat unclear.

TABLE 12

Broth Treatments

| Organism[1] | Broth | Plating Media |
|---|---|---|
| S. sonnei | Nutrient Broth | Nutrient Agar |
| L. monocytogenes | Brain Heart Infusion Broth | Brain Heart Infusion Agar |
| E. coli | Brain Heart Infusion Broth | Brain Heart Infusion Agar |
| S. enteritidis | Tryptic Soy Broth | Tryptic Soy Agar |
| P. aeruginosa | Tryptic Soy Broth | Tryptic Soy Agar |
| C. jejuni | Brucella Broth | Brucella Agar |

[1]Shigella sonnei, Listeria monocytogenes, Escherichia coli, Salmonella enteritidis, Pseudomonas aeruginosa, and Campylobacter jejuni.

The microbiocidal solution of this invention was prepared in the following manner:

1. To form a stock solution, 100 g of 1,3-dibromo-5,5-dimethylhydantoin (DBDMM) was stirred into 10 liters (10,000 mL) of water for 20 minutes. After filtration, the resulting clear solution contains 1300 mg per liter as $Br_2$. This corresponds to 580 mg per liter (or 580 ppm $Cl_2$) when expressed as $Cl_2$.
2. The chill water solution of DBDMH having a content of 10 ppm of $Cl_2$ equivalent was formed by mixing 175 mL of the above stock solution with 10 liters (10,000 mL) of the above prepared chicken chill water solution. The chill water solution of DBDMH containing 20 ppm $Cl_2$ equivalent and 150 ppm $Cl_2$ equivalent were prepared in the same manner except that 350 mL of the above stock solution were mixed with another 10-liter portion of the above prepared chicken chill water solution.

Table 13 shows the composition of the "chicken soup" used in these tests.

TABLE 13

Composition of "Chicken Soup"

| Material[1] | Material per 2100 mL[2] |
|---|---|
| Water Added | 1840 mL |
| Bacteria Stock Solution | 200 mL |
| Blood | 40 mL |
| Chicken Abdominal Fat (ground) | 30 g |
| Thigh Meat Particles | 30 g |
| Chicken skin with fat | 10 g |
| TOTAL | 2100 mL equivalent |

[1]The combined material was chilled overnight.
[2]The material was ground and aggressively stirred prior to use.

The procedure used for whole bird wash sampling was as follows:
1. All samples were kept at ≦50 degrees Fahrenheit following collection.
2. Microbiological analyses of samples began within 24 hours of sample collection.
3. Information on the individual sample identification, date of collection, time of collection (phase during shift), treatment group and location of sample point were recorded on each sample bottle.
4. At each defined sample time, carcasses were taken individually from the processing line wearing latex or rubber gloves. The gloves were rinsed with alcohol between each collection.
5. Any excess fluid was drained off from the carcass. Each individual carcass was transferred to a sterile stomacher bag.
6. To each carcass contained in the sterile stomacher bag, 400 mL of Butterfield's Phosphate Diluent (BPD) was added while making sure to pour the BPD into the inside of the carcass cavity. The carcass was rinsed inside and out with a rocking motion for one minute (ca. 35 RPM). This was best done by grasping the broiler carcass with one hand and the closed top of the bag with the other then rocking with a reciprocal motion in a 18–24 inch arc, assuring that all surfaces (interior and exterior of the carcass) were rinsed.
7. The rinse solutions from each stomacher bag was transferred into the sample bottles, taking care to ensure that the information on the date of collection, time of collection (phase during shift), treatment group and location of sampler point matched that of the sample.
8. Each bottle was sealed with parafilm and placed into a styrene container with crushed or dry ice or frozen freezer packs for overnight delivery to a testing laboratory.
9. All filled styrene containers were held in a chilled (not below freezing) area until within 1 to 2 hours of courier collection for shipment.

Quantitative or qualitative determinations for bacterial organisms were conducted according to the following methodologies: Aerobic plate counts—Counting rules according to BAM 8th ed., Chapter 3. Coliform and *E. coli* counts—AOAC, 991.14, Petrifilm. *Salmonella*—AOAC 986.35, ELISA presumptive screen. *Salmonella*—USDA LC-75, incidence. *Campylobacter*—USDA LC-69, incidence. *Listeria*—USDA LC-57, incidence.

In greater detail the trial events and experimental design used in this group of tests were as follows:
a) Test microorganisms used were: *Escherichia coli* ATCC 11229 *Pseudomonas aeruginosa* ATCC 15442 *Salmonella enteritidis* ATCC 13076 *Shigella sonnei* ATCC 9290 *Listeria monocytogenes* ATCC 7644 *Campylobacter jejuni* ATCC 29428
b) Test Procedure: All test strains were grown individually at 35° C. for 24 hours in the media specified in Table 12. Cells were harvested by centrifugation at 10,000×g for 10 minutes and washed twice with Butterfield's Phosphate Buffer (BPB of pH 7.2). Cells were resuspended in BPB to obtain a cell suspension of approximately $1.0 \times 10^8$ CFU/mL for each microorganism. The target inoculum levels were approximately $10^6$ CFU/mL in the final test solutions. In the cases of *S. enteritidis* and *P. aeruginosa* the species were washed by pouring into prepared sterile centrifuge tubes with cheesecloth filters. The culture was then pelleted and washed using above techniques and repeated 3 times.
c) The birds (56 days old) were processed under normal commercial conditions.
d) The bacteria were added to a large batch of the "chicken soup", and then aliquots of the resultant mixture were distributed equally among the chill waters used for each test. Then the particular disinfectant composition under test was added to one of the chill waters. The chill waters each contained $10^4$ per mL *Escherichia coli*, $10^4$ per mL *Salmonella enteritidis*, 104 per mL *Campylobacter jejuni*, and $10^4$ per mL spoilage bacteria each from three strains (*Listeria monocytogenes, Pseudomonas aeruginosa*, and *Shigella sonnei*).
e) Birds were added to each of ten 50-gallon containers containing these respective treatments (or control) and were kept in the containers for the 1.5 hour chilling period.
f) During the 1.5 hour chilling period, the contents were vigorously stirred every 10 minutes.
g) After the 1.5 hour chilling period, the whole birds were placed in individual sterile stomacher bags and the whole bird rinse (as described above) was conducted and samples of the rinse were placed on the appropriate agar plates. The plates were placed in the incubator for 24 hours at 37° C. Then the plates were read after 24 hours to determine total count on each plate.

The results of this group of tests are summarized in Tables 14 and 15.

TABLE 14

| | Whole Bird Total Aerobic Bacteria (% Reduction)[1] | | |
|---|---|---|---|
| Water Treatment | Water pH 7 | Water pH 8 | Water pH 9 |
| None (Control) | — | — | — |
| Clorox ® Bleach (20 ppm Cl$_2$ equivalent) | 15% | 15% | 2% |
| Aquatize ® biocide (1:500 dilution) | 76% | 71% | 64% |
| Aquatize ® biocide (1:1000 dilution) | 42% | 45% | 33% |
| DBDMH (10 ppm Cl$_2$ equivalent) | 85% | 82% | 78% |
| DBDMH (20 ppm Cl$_2$ equivalent) | 99% | 98% | 96% |

[1]Each value represents 50 birds per treatment.

TABLE 15

| | Disinfecting Treatment (average bacteria count per bird)[2,3] | | | |
|---|---|---|---|---|
| Organism[1] | Control | Clorox Bleach (20 ppm) | DBDMH (10 ppm) | DBDMH (20 ppm) |
| S. sonnei | 4551 | 3552 | 456 | 12 |
| L. monocytogenes | 2463 | 2065 | 262 | 6 |

TABLE 15-continued

|  | Disinfecting Treatment (average bacteria count per bird)[2,3] | | | |
|---|---|---|---|---|
| Organism[1] | Control | Clorox Bleach (20 ppm) | DBDMH (10 ppm) | DBDMH (20 ppm) |
| E. coli | 3055 | 2759 | 357 | 4 |
| S. enteritidis | 3969 | 3160 | 560 | 10 |
| P. aeruginosa | 2783 | 2280 | 289 | 9 |
| C. jejuni | 1282 | 981 | 183 | 15 |
| Mean % Reduction From Control | — | 18.3% | 85.8% | 98.8% |

[1]*Escherichia coli, Salmonella enteritidis, Pseudomonas aeruginosa, Campylobacter jejuni, listeria monocytogenes,* and *Shigella sonnei*
[2]NOTE: Cross contamination is more likely in a processing environment where birds were processed and samples taken for individual culture determination.
[3]Each value represents 25 birds per treatment.

Example 4

A study was conducted to determine the effect of Clorox® bleach, and 1,3-dibromo-5,5-dimethylhydantoin (DBDMH) on carcass bacteria residual after 1.5 hour in a chill tank solution and spoilage 20-day shelf life longevity (caused by bacteria contamination). Tests were conducted at pH 8 (adjusted by trisodium phosphate). Skin pigmentation (Minolta Color Meter L value or Lightness, a value or redness and b value or yellowness) were determined before and post-processing.

In general the study involved normal processing of 56-day-old birds, immersing carcasses first in a warm bath containing $10^4$ per mL *Escherichia coli*, $10^4$ per mL *Sailmonella enteritidis*, 10 per mL *Pseudomonas aeruginosa*, $10^4$ per mL *Campylobacter jejuni*, and $10^4$ per mL spoilage bacteria each from three strains (*Listeria monocytogenes* and *Shigella sonnel*). Carcass were then immersed in a chill tank "soup", containing normal organic fluids (blood, fat, skin, and meat particles) and containing various disinfectants (termed test materials).

Four test groups of birds were tested at pH 8 for whole bird bacteria counts. Table 16 sets forth the experimental design for these whole bacteria count tests.

TABLE 16

| Test Group | Test Material (Chill Tank) | Reps | Birds/Rep |
|---|---|---|---|
| 1 | None (Control) | 6 | 10 |
| 2 | Clorox ® bleach (20 ppm Cl$_2$ equivalent) | 6 | 10 |
| 3 | DBDMH (10 ppm Cl$_2$ equivalent) | 6 | 10 |
| 4 | DBDMH (20 ppm Cl$_2$ equivalent) | 6 | 10 |

A DBDMH stock solution and test solutions, a bacteria stock solution, and a "chicken soup" were prepared as in Example 3. In addition, the bacterial broth treatments, the whole bird wash sampling procedure, and the methodologies used for quantitative or qualitative determinations for bacterial organisms were conducted as in Example 3.

In greater detail the trial events and experimental design used in this group of tests were as follows:

a) Test microorganisms used were: *Escherichia coli* ATCC 11229 *Pseudomonas aeruginosa* ATCC 15442 *Salmonella enteritidis* ATCC 13076 *Shigella sonnei* ATCC 9290 *Listeria monocytogenes* ATCC 7644 *Campylobacter jejuni* ATCC 29428 b) Test Procedure: All test strains were grown individually at 35° C. for 24 hours in the media specified in Table 12. Cells were harvested by centrifugation at 10,000×g for 10 minutes and washed twice with Butterfield's Phosphate Buffer (BPB of pH 7.2). Cells were resuspended in BPB to obtain a cell suspension of approximately $1.0 \times 10^8$ CFU/mL for each microorganism. The target inoculum levels were approximately $10^6$ CFU/mL in the final test solutions. In the cases of *S. enteritidis* and *P. aeruginosa* the species were washed by pouring into prepared sterile centrifuge tubes with cheesecloth filters. The culture was then pelleted and washed using above techniques and repeated 3 times.

c) The birds (56 days old) were processed under normal commercial conditions.

d) The bacteria were added to a large batch of the "chicken soup", and then aliquots of the resultant mixture were distributed equally among the chill waters used for each test. Then the particular disinfectant composition under test was added to one of the chill waters. The chill waters each contained $10^4$ per mL *Escherichia coli*, $10^4$ per mL *Salmonella enteritidis*, $10^4$ per mL *Campylobacter jejuni*, and $10^4$ per mL spoilage bacteria each from three strains (*Listeria monocytogenes, Pseudomonas aeruginosa*, and *Shigella sonnei*).

e) Birds were added to each of ten 50-gallon containers containing these respective treatments (or control) and were kept in the containers for the 1.5 hour chilling period.

f) During the 1.5 hour chilling period, the contents were vigorously stirred every 10 minutes.

g) After the 1.5 hour chilling period, the whole birds were placed in a commercial refrigerator for 20 days of storage.

h) Skin pigmentation (using Minolta Color Meter L or Lightness, a or redness and b or yellowness) were determined on all birds before and immediately after post-processing chilling.

i) For Day 0, a total of 5 whole birds per treatment were randomly chosen from each treatment and placed in individual sterile stomacher bag and the whole bird rinse (as described in Example 3) was carried out and samples of the rinse were placed on appropriate agar plates.

j) For each of succeeding days 2, 4, 6, 8, 10, 12, 14, 16, 18, and 20, a total of 5 whole birds per treatment were randomly chosen from each treatment and placed in individual sterile stomacher bags and the whole bird rinse (as described in Example 3) was conducted and samples of the rinse were placed on the appropriate agar plates.

k) All of the treated agar plates were placed in an incubator for 24 hours at 35° C. Plates were read after 24 hours to determine total count on each plate.

The results of these tests are summarized in Tables 17–30.

TABLE 17

| Water Treatment | Percentage of Total Bacteria Reduction From Control (Days post-processing) | | | | | | | | | | |
|---|---|---|---|---|---|---|---|---|---|---|---|
| | Day 0 | Day 2 | Day 4 | Day 6 | Day 8 | Day 10 | Day 12 | Day 14 | Day 16 | Day 18 | Day 20 |
| None (Control) | — | — | — | — | — | — | — | — | — | — | — |
| Clorox ® Bleach (20 ppm) | 22.5 | 23.1 | 22.2 | 25.2 | 26.0 | 25.7 | 25.9 | 26.5 | 23.2 | 23.12 | 20.5 |
| DBDMH (10 ppm) | 77.8 | 77.3 | 76.8 | 77.1 | 74.6 | 71.9 | 69.2 | 66.2 | 61.9 | 58.5 | 53.7 |
| DBDMH (20 ppm) | 99.5 | 99.4 | 99.2 | 98.5 | 97.3 | 95.1 | 91.2 | 84.3 | 71.2 | 68.0 | 67.2 |

TABLE 18

| Water Treatment | Average skin TBA Values[1] (Days post-processing) | | | | | | | | | | |
|---|---|---|---|---|---|---|---|---|---|---|---|
| | Day 0 | Day 2 | Day 4 | Day 6 | Day 8 | Day 10 | Day 12 | Day 14 | Day 16 | Day 18 | Day 20 |
| None (Control) | 0.14a | 0.31a | 0.45a | 0.69a | 0.88a | 1.23a | 1.36a | 1.66a | 2.08a | 2.39a | 3.02a |
| Clorox ® Bleach (20 ppm) | 0.10a | 0.42a | 0.68a | 0.72a | 0.90a | 1.10a | 1.49a | 1.73a | 2.19a | 2.51a | 2.88a |
| DBDMH (10 ppm) | 0.20a | 0.54a | 0.79a | 0.54a | 0.76a | 1.20a | 1.77a | 1.94a | 2.33a | 2.45a | 2.92a |
| DBDMH (20 ppm) | 0.22a | 0.36a | 0.46a | 0.71a | 0.75a | 1.22a | 1.53a | 1.87a | 2.19a | 2.68a | 2.73a |

[1] NOTE: Means within a row without a common superscript are significantly different ($P < 0.05$) as determined by Least Significant Difference.

TABLE 19

| Water Treatment | Skin Pigmentation Value Minolta Color Meter[1] | | | | | |
|---|---|---|---|---|---|---|
| | Mean Pre-Chill Minolta Value | | | Mean Post-Chill Minolta Value | | |
| | L | a | b | L | a | b |
| None (Control) | 62.84 a | 5.32 a | 15.42 a | 58.84 a | 5.93 a | 16.84 a |
| Clorox ® Bleach (20 ppm) | 63.62 a | 5.49 a | 15.94 a | 58.84 a | 5.64 a | 16.16 a |
| DBDMH (10 ppm) | 61.55 a | 5.14 a | 15.63 a | 58.84 a | 6.09 a | 16.22 a |
| DBDMH (20 ppm) | 60.77 a | 5.69 a | 15.67 a | 58.84 a | 6.24 a | 16.37 a |

[1] NOTE: Means within a row without a common superscript are significantly different ($P < 0.05$) as determined by Least Significant Difference.

TABLE 20

Effect of Disinfection Treatment on Day 0

| Organism | Disinfecting Treatment (average bacteria count per bird) | | | |
|---|---|---|---|---|
| | Control | Clorox bleach (20 ppm) | DBDMH (10 ppm) | DBDMH (20 ppm) |
| S. sonnei | 3687 | 2948 | 845 | 8 |
| L. monocytogenes | 2569 | 2281 | 528 | 13 |
| E. coli | 3879 | 2310 | 861 | 22 |
| S. enteritidis | 1678 | 1064 | 292 | 12 |
| P. aeruginosa | 2974 | 2681 | 743 | 6 |
| C. jejuni | 2276 | 1935 | 519 | 17 |
| Mean % Reduction From Control | — | 22.5% | 77.8% | 99.5% |

TABLE 21

Effect of Disinfection Treatment on Day 2

| Organism | Disinfecting Treatment (average bacteria count per bird) | | | |
|---|---|---|---|---|
| | Control | Clorox (20 ppm) | DBDMH (10 ppm) | DBDMH (20 ppm) |
| S. sonnei | 4119 | 3241 | 962 | 12 |
| L. monocytogenes | 2749 | 2442 | 601 | 19 |
| E. coli | 4193 | 2604 | 966 | 31 |
| S. enteritidis | 1921 | 1191 | 344 | 18 |
| P. aeruginosa | 3313 | 2889 | 820 | 9 |
| C. jejuni | 2534 | 2114 | 573 | 25 |
| Mean % Reduction From Control | — | 23.1% | 77.3% | 99.4% |

TABLE 22

Effect of Disinfection Treatment on Day 4

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 4664 | 3528 | 1101 | 19 |
| L. monocytogenes | 2920 | 2751 | 670 | 28 |
| E. coli | 4379 | 3001 | 1050 | 49 |
| S. enteritidis | 2152 | 1309 | 394 | 27 |
| P. aeruginosa | 3592 | 3127 | 931 | 13 |
| C. jejuni | 2830 | 2267 | 627 | 39 |
| Mean % Reduction From Control | — | 22.2% | 76.8% | 99.2% |

TABLE 23

Effect of Disinfection Treatment on Day 6

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 5424 | 3802 | 1288 | 37 |
| L. monocytogenes | 3176 | 3071 | 741 | 55 |
| E. coli | 4769 | 3142 | 1124 | 100 |
| S. enteritidis | 2426 | 1347 | 433 | 55 |
| P. aeruginosa | 4141 | 3454 | 1013 | 25 |
| C. jejuni | 3113 | 2423 | 671 | 78 |
| Mean % Reduction From Control | — | 25.2% | 77.1% | 98.5% |

TABLE 24

Effect of Disinfection Treatment on Day 8

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 5969 | 4008 | 1604 | 76 |
| L. monocytogenes | 3407 | 3474 | 880 | 107 |
| E. coli | 5194 | 3438 | 1364 | 204 |
| S. enteritidis | 2764 | 1519 | 507 | 104 |
| P. aeruginosa | 4768 | 3798 | 1268 | 48 |
| C. jejuni | 3353 | 2594 | 834 | 157 |
| Mean % Reduction From Control | — | 26.0% | 74.6% | 97.3% |

TABLE 25

Effect of Disinfection Treatment on Day 10

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 6292 | 4415 | 1954 | 156 |
| L. monocytogenes | 3854 | 3767 | 1096 | 218 |
| E. coli | 5683 | 3694 | 1621 | 401 |
| S. enteritidis | 3116 | 1605 | 616 | 212 |
| P. aeruginosa | 5243 | 4305 | 1485 | 91 |
| C. jejuni | 3589 | 2844 | 1043 | 294 |
| Mean % Reduction From Control | — | 25.7% | 71.9% | 95.1% |

TABLE 26

Effect of Disinfection Treatment on Day 12

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 6890 | 5030 | 2347 | 323 |
| L. monocytogenes | 4348 | 4195 | 1335 | 442 |
| E. coli | 6316 | 3902 | 2063 | 775 |
| S. enteritidis | 3461 | 1819 | 740 | 413 |
| P. aeruginosa | 5743 | 4720 | 1730 | 186 |
| C. jejuni | 4133 | 3213 | 1309 | 594 |
| Mean % Reduction From Control | — | 25.9% | 69.2% | 91.2% |

TABLE 27

Effect of Disinfection Treatment on Day 14

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 7768 | 5313 | 2848 | 657 |
| L. monocytogenes | 4781 | 4755 | 1564 | 843 |
| E. coli | 6762 | 4279 | 2581 | 1453 |
| S. enteritidis | 3901 | 2055 | 919 | 832 |
| P. aeruginosa | 6426 | 5200 | 2055 | 363 |
| C. jejuni | 4454 | 3446 | 1551 | 1191 |
| Mean % Reduction From Control | — | 26.5% | 66.2% | 84.3% |

TABLE 28

Effect of Disinfection Treatment on Day 16

Disinfecting Treatment
(average bacteria count per bird)$^2$

| Organism$^1$ | Control | Clorox (20 ppm) | DBDMH (10 ppm) | DBDMH (20 ppm) |
|---|---|---|---|---|
| S. sonnei | 7970 | 6108 | 3513 | 1286 |
| L. monocytogenes | 5263 | 5228 | 1901 | 1646 |
| E. coli | 7201 | 4692 | 3005 | 2933 |
| S. enteritidis | 4281 | 2328 | 1081 | 1711 |
| P. aeruginosa | 6969 | 6005 | 2560 | 700 |
| C. jejuni | 4898 | 3733 | 1880 | 2259 |
| Mean % Reduction From Control | — | 23.2% | 61.9% | 71.2% |

TABLE 29

Effect of Disinfection Treatment on Day 18

| | | Disinfecting Treatment (average bacteria count per bird)[2,3] | | |
|---|---|---|---|---|
| Organism[1] | Control | Clorox (20 ppm) | DBDMH (10 ppm) | DBDMH (20 ppm) |
| S. sonnei | 9004 | 6957 | 4242 | 1604 |
| L. monocytogenes | 5799 | 5694 | 2221 | 1985 |
| E. coli | 7725 | 5097 | 3617 | 3645 |
| S. enteritidis | 4835 | 2613 | 1286 | 2074 |
| P. aeruginosa | 7814 | 6869 | 3087 | 826 |
| C. jejuni | 5319 | 3900 | 2359 | 2835 |
| Mean % Reduction From Control | — | 23.1% | 58.5% | 68.0% |

TABLE 30

Effect of Disinfection Treatment on Day 20

| | | Disinfecting Treatment (average bacteria count per bird)[2,3] | | |
|---|---|---|---|---|
| Organism[1] | Control | Clorox (20 ppm) | DBDMH (10 ppm) | DBDMH (20 ppm) |
| S. sonnei | 9288 | 7409 | 4941 | 1834 |
| L. monocytogenes | 6419 | 6506 | 2678 | 2238 |
| E. coli | 8272 | 5635 | 4460 | 4036 |
| S. enteritidis | 5335 | 2976 | 1513 | 2258 |
| P. aeruginosa | 8604 | 7886 | 3853 | 908 |
| C. jejuni | 5789 | 4332 | 2789 | 3059 |
| Mean % Reduction From Control | — | 20.5% | 53.7% | 67.2% |

In Tables 19–30 each figure on average bacteria count per bird represents the average of 5 birds.

Example 5

The objective of this study was to determine the effect of bleach microbiocidal control (20 ppm $Cl_2$ equivalent) and of microbiocidal control with 1,3-dibromo-5,5-dimethylhydantoin (DBDMH) on organoleptic taste evaluation of both breast and thigh meat. Formal trained taste panel evaluation was conducted. The trial was conducted using 49-day old birds which were processed unchallenged with external sources of bacteria and under sterile conditions.

A total of 120 birds were used in this study. Sixty of the birds served as a control group. These were subjected to treatment in a chill tank containing Clorox® bleach at a 20 ppm $Cl_2$ equivalent level. The other 60 birds were treated in a chill tank in the same fashion except that the chilling water contained DBDMH at the level of 20 ppm $Cl_2$ equivalent. During the 1.5 hour chilling period in the chill tank, the contents of the tank were vigorously stirred every 10 minutes. After the 1.5 hour chilling period, the whole birds were individually bagged and placed in a commercial refrigerator for 20 days of storage. After aging, individual breast and thigh samples were cut and cooked to an internal temperature of 190° F. Taste evaluation was determined using 10 trained taste panel experts. A Ranking System ("1" or "2") was used where "1" represents the better tasting sample. A simple average of subject evaluations or rankings per person were used. Statistical evaluation was employed by using each subject as a block employed delta 0.05.

Tables 31 and 32 set forth the results of these taste evaluations.

TABLE 31

Effect of Chill Tank Water Treatment On Taste Preference (Breast Meat Evaluation)

| Water Treatment | SUMMARY - Tasting Ranking[1] | | | | | | | | | | |
|---|---|---|---|---|---|---|---|---|---|---|---|
| | S1 | S2 | S3 | S4 | S5 | S6 | S7 | S8 | S9 | S10 | Mean[2] |
| None (20 ppm $Cl_2$ equivalent bleach control) | 2 | 1 | 1 | 1 | 2 | 1 | 1 | 2 | 1 | 2 | 1.4a |
| DBDMH (20 ppm $Cl_2$ equivalent) | 1 | 2 | 2 | 2 | 1 | 2 | 2 | 1 | 2 | 1 | 1.6a |

[1]S(subject) = trained taste panelist subject number.
[2]NOTE: Means within a row without a common superscript are significantly different (P < 0.05) as determined by Least Significant Difference.

TABLE 32

Effect of Chill Tank Water Treatment On Taste Preference (Thigh Meat Evaluation)

| Water Treatment | SUMMARY - Tasting Ranking[1] | | | | | | | | | | |
|---|---|---|---|---|---|---|---|---|---|---|---|
| | S1 | S2 | S3 | S4 | S5 | S6 | S7 | S8 | S9 | S10 | Mean[2] |
| None (20 ppm $Cl_2$ equivalent bleach control) | 1 | 2 | 2 | 1 | 1 | 2 | 2 | 2 | 1 | 2 | 1.6a |
| DBDMH (20 ppm $Cl_2$ equivalent) | 2 | 1 | 1 | 2 | 2 | 1 | 1 | 1 | 2 | 1 | 1.4a |

[1]S(subject) = trained taste panelist subject number.
[2]NOTE: Means within a row without a common superscript are significantly different (P < 0.05) as determined by Least Significant Difference.

Example 6

The objective of this study was to determine the effect of Clorox® bleach and 1,3-dibromo-5,5-dimethylhydantoin (DBDMH) on individual carcass bacteria field strains after 1.5 hour in a chill tank solution and spoilage 20-day shelf life longevity (caused by bacteria contamination) in a Graded Level Study Model. After normal processing of 56-day-old birds, carcasses were immersed first in a warm bath containing $10^4$ CFU's per mL Escherichia coli, $10^4$ CFU's per mL Salmonella enterilidis, $10^4$ CFUs per mL Pseudomonas aeruginosa, $10^4$ CFU's per mL Campylobacter jejuni, and $10^4$ CFU's per mL spoilage bacteria each from two strains (Listeria monocytogenes and Shigella sonnei). Carcasses were then immersed in a chill tank "soup", containing normal organic fluids (blood, fat, skin, and meat particles) and containing various disinfectants (termed test materials). These tests were conducted at pH 8 (adjusted by trisodium phosphate). Skin pigmentation (Minolta Color Meter L value or Lightness, a value or redness and b value or yellowness) was determined before and after processing. Post-chilling skin bacteria of various strains were determined over a 20-day period. Sensory evaluation was determined to demonstrate spoilage times and shelf-life. After salmonella infection in chill tanks, USDA HACCP salmonella detection was simulated and reported.

The materials tested and the experimental design of these test were as summarized in Table 33.

TABLE 33

| Test Group | Test Material (Chill Tank) | Reps | Birds/ Rep |
|---|---|---|---|
| 1 | None (Control) | 10 | 12 |
| 2 | Clorox ® bleach (20 ppm $Cl_2$ equivalent | 10 | 12 |
| 3 | DBDMH (5 ppm $Cl_2$ equivalent) | 10 | 12 |
| 4 | DBDMH (10 ppm $Cl_2$ equivalent) | 10 | 12 |
| 5 | DBDMH (15 ppm $Cl_2$ equivalent) | 10 | 12 |
| 6 | DBDMH (20 ppm $Cl_2$ equivalent) | 10 | 12 |
| 7 | DBDMH (25 ppm $Cl_2$ equivalent) | 10 | 12 |

A DBDMM stock solution and DBDMH test solutions of the concentrations specified in Table 33, a bacteria stock solution, and a "chicken soup" were prepared as in Example 3. In addition, the bacterial broth treatments, the whole bird wash sampling procedure, and the methodologies used for quantitative or qualitative determinations for bacterial organisms were conducted as in Example 3.

The trial events and experimental design used in this group of tests were the same as in Example 5 with the following exceptions:

a) The temperature during the 20-day period of storage in the refrigerator was 40° F.
b) Observations of the degree of "bloating" (defined as water or air additions under the skin area considered objectionable) were conducted on all processed birds.
c) On each of sampling days 0, 2, 4, 6, 8, 10, 12, 14, 16, 18, and 20, ten carcasses from each treatment were analyzed by removing 23.8 $cm^2$ of skin from the breast right up to the neck using a template and a sterile scalpel. Each skin sample was placed in a bag with 15 mL Butterfield's Phosphate Buffer Solution (BPBS) added and treated in a Stomacher bag for 60 seconds. A 10-fold dilution series of the mixture was made in BPBS and two parallel samples of 20 mL each were spread on the appropriate plate count agar for determination of the total viable numbers. The plates were incubated at 35° C. for 24 hours. Mean values were calculated from the two determinations of the three samples taken from each combination of chilling and storage. Bacterial numbers were reported as pooled or averaged $log_{10}$ colony-forming units (CFU's) per square centimeter.
d) Also on sampling day 0, 102 total of the remaining 110 carcasses from each treatment (all bloating and oddly processed birds were removed) were "whole bird" washed by the sampling procedure described in Example 3. *Salmonella* detection were noted and reported as number of positive *salmonella* colonies per 51 birds and % of total. Tables 34–37 summarize the results of this group of tests.

TABLE 34

| Water Treatment | Salmonella Positive Samples (Number per 51)[1] (Birds were inoculated with Salmonella prior to chilling) |
|---|---|
| None (Control) | 32/51 (62.74%) |
| Clorox ® Bleach (20 ppm) | 11/51 (22.57%) |
| DBDMH (5 ppm) | 7/51 (13.73%) |
| DBDMH (10 ppm) | 4/51 (7.84%) |
| DBDMH (15 ppm) | 2/51 (3.92%) |
| DBDMH (20 ppm) | 1/51 (1.96%) |
| DBDMH (25 ppm) | 0/51 (0.00%) |

[1]Twelve (12) per 51 or less is considered to be statistically acceptable by USDA HACCP standards. A total of 102 birds were used to determine salmonella positive samples and a simple average determined.

TABLE 35

| Water Treatment | Birds (Number per 60 birds processed)[1] |
|---|---|
| None (Control) | 1/120 (0.83%) |
| Clorox ® Bleach (20 ppm) | 0/120 (0.00%) |
| DBDMH (5 ppm) | 2/120 (1.67%) |
| DBDMH (10 ppm) | 0/120 (0.00%) |
| DBDMH (15 ppm) | 1/120 (0.83%) |
| DBDMH (20 ppm) | 0/120 (0.00%) |
| DBDMH (25 ppm) | 1/120 (0.83%) |

[1]Four (4) or more per treatment is considered to be highly objectionable.

TABLE 36

| Water Treatment | Sensory Score (days post-processing)[1,2] | | | |
|---|---|---|---|---|
| | 5 days | 10 days | 15 days | 20 days |
| None (Control) | 5.6 c | 7.3 c | 8.2 c | 9.0 d |
| Clorox ® bleach (20 ppm) | 3.8 b | 3.6 b | 5.5 b | 7.1 c |
| DBDMH (5 ppm) | 2.4 ab | 3.2 b | 3.9 a | 5.6 a |
| DBDMH (10 ppm) | 1.9 ab | 2.3 a | 3.4 a | 4.8 a |
| DBDMH (15 ppm) | 1.3 a | 2.1 a | 2.6 a | 4.9 a |
| DBDMH (20 ppm) | 1.1 a | 1.8 a | 2.7 a | 4.3 a |
| DBDMH (25 ppm) | 1.4 a | 2.1 a | 2.3 a | 4.6 a |

[1]Continuous scale for non-structured fresh inside carcass odor sensory attributes ranges from value 1.0 (the lowest intensity) to value 9.0 (the highest intensity). NOTE: Means within a row without a common superscript are significantly different (P < 0.05) as determined by Least Significant Difference.
[2]Five (5) or more is considered to be highly objectionable.

TABLE 37

| Water Treatment | Skin Pigmentation[1] | | | | | |
|---|---|---|---|---|---|---|
| | Mean Pre-Chill Minolta Value[2] | | | Mean Post-Chill Minolta Value[2] | | |
| | L | a | B | L | a | b |
| None (Control) | 59.72 a | 4.34 a | 13.67 a | 51.84 a | 5.12 a | 15.27 a |
| Clorox ® Bleach (20 ppm) | 60.76 a | 4.93 a | 13.74 a | 55.81 a | 5.08 a | 15.49 a |
| DBDMH (5 ppm) | 58.80 a | 4.67 a | 13.61 a | 52.68 a | 5.42 a | 15.64 a |
| DBDMH (10 ppm) | 59.97 a | 4.31 a | 13.64 a | 53.19 a | 5.69 a | 15.75 a |
| DBDMH (15 ppm) | 58.43 a | 4.84 a | 13.81 a | 54.21 a | 5.55 a | 15.64 a |
| DBDMH (20 ppm) | 58.54 a | 4.99 a | 13.67 a | 53.74 a | 5.49 a | 15.80 a |
| DBDMH (25 ppm) | 58.97 a | 4.68 a | 13.50 a | 54.25 a | 5.63 a | 15.76 a |

[1]NOTE: Means within a row without a common superscript are significantly different (P < 0.05) as determined by Least Significant Difference.
[2]Skin pigmentation (Minolta Color Meter L value or Lightness, a value or redness and b value or yellowness).

Figure 2:
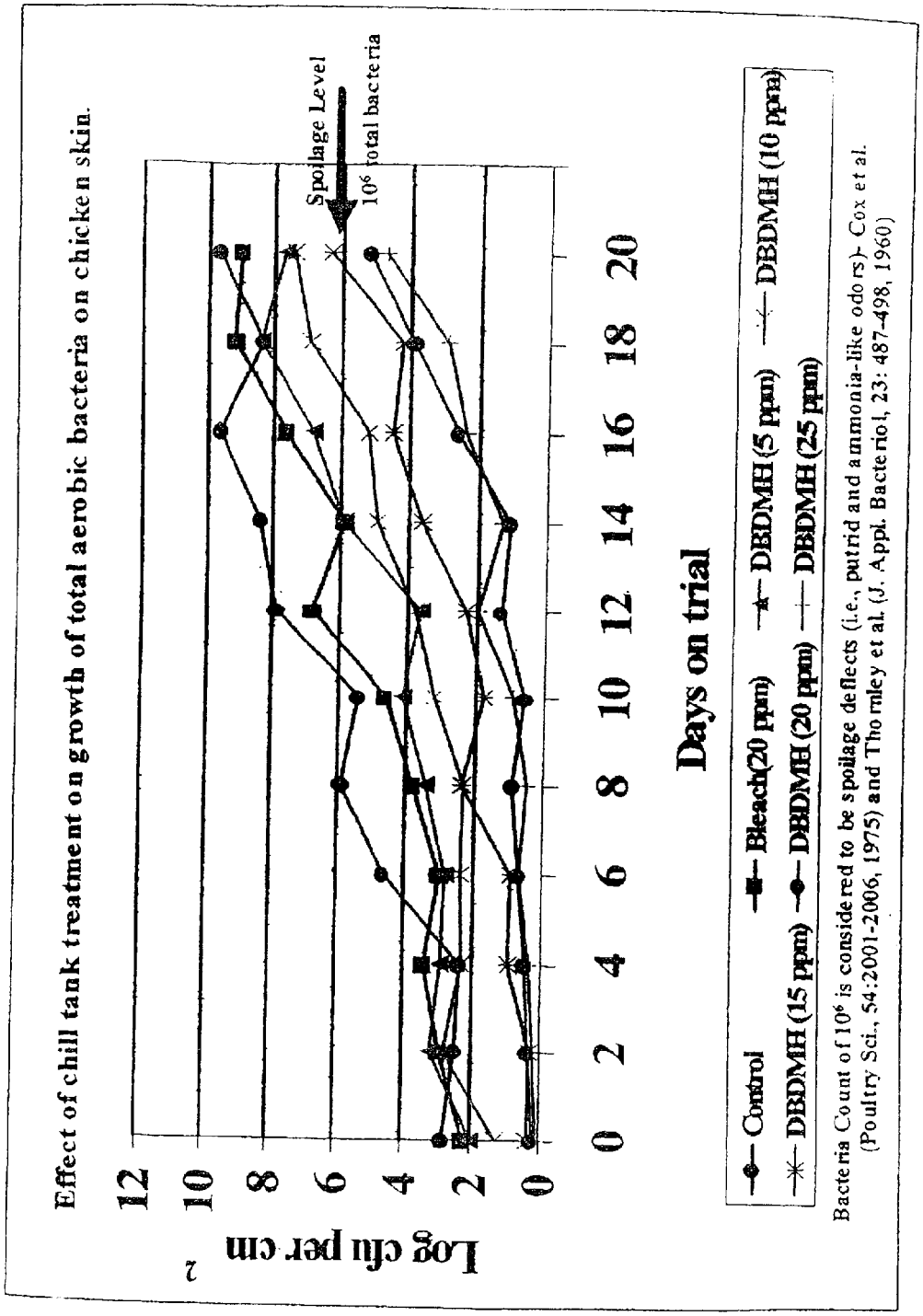
FIG. 2 is a graphical depiction of the effect of chill tank microbiocidal treatments on growth of total aerobic bacteria on chicken skin.

Results from the above tests on the effect of chill tank treatment on growth of *Pseudomonas* species on the chicken skin are graphically depicted in FIG. 1. FIG. 2 depicts graphically the results of the above tests on the effect of chill tank treatment on growth of total aerobic bacteria on the chicken skin.

Example 7

A study was carried out to determine the effectiveness of several microbiocidal compounds of this invention, as well as sodium hypochlorite when used as carcass rinses. The microbiocides of this invention used in this study were 1,3-dibromo-5,5-dimethylhy-dantoin (DBDMH), N,N'-bromochloro-5,5-dimethylhydantoin (BCDMH) and Stabrom® 909 biocide (Albemarle Corporation), a concentrated alkaline aqueous solution produced from bromine chloride and sulfamate anion (SSBC).

After normal processing of 56 day-old birds, carcasses were immersed first in a warm bath containing $10^4$ per mL *Escherichia coli*, $10^4$ per mL *Salmonella enteritidis*, $10^4$ per mL *Pseudomonas aeruginosa*, $10^4$ per mL *Campylobacter jejuni*, and $10^4$ per mL spoilage bacteria each from two strains (*Listeria monocytogenes* and *Shigella sonnei*). Carcasses were then immersed in a chill tank "soup", containing normal organic fluids blood, fat, skin, and meat particles) and containing various disinfectants (termed test materials). These whole bird bacteria count tests were conducted at pH 8. The effect of the test compounds on skin pigmentation was determined by use of Minolta Color Meter L value or Lightness, a value or redness and b value or yellowness. Post-chilling skin bacteria of various strains were determined over a 20-day period. Spoilage, using sensory odors as a model, determined time required to create a putrid/ammonia-like odor. After *salmonella* infection in chill tanks, USDA HACCP *salmonella* detection was simulated and reported. Table 38 describes the test material dosages and overall design of this group of tests.

TABLE 38

| Test Group | Test Material (Chill Tank) | Reps | Birds/Rep |
|---|---|---|---|
| 1 | None (Control) | 10 | 12 |
| 2 | Clorox ® bleach (20 ppm Cl$_2$ equivalent) during chilling | 10 | 12 |
| 3 | DBDMH (20 ppm Cl$_2$ equivalent) during chilling | 10 | 12 |
| 4 | BCDMH (20 ppm Cl$_2$ equivalent) during chilling | 10 | 12 |
| 5 | SSBC carcass spray (3% liquid pre-chill application) | 1 | 10 |

DBDMH and BCDMH stock solutions and diluted test solutions (20 ppm Cl$_2$ equivalent), a bacteria stock solution, and a "chicken soup" were prepared as in Example 3 except that the Stabrom® 909 biocide concentrate was diluted by adding 30 mL per liter of water just prior to application. This diluted solution was sprayed on the birds, both inside and outside, in quantities of 200 mL per bird. In addition, the bacterial broth treatments, the whole bird wash sampling procedure, and the methodologies used for quantitative or qualitative determinations for bacterial organisms were conducted as in Example 3.

The details concerning the trial events used as well as the detailed experimental design used in these tests were the same as described in Example 6. The only exceptions
a) In the case of the birds of Test Group 5 (note Table 38), while the carcass was still warm, the 10 birds were each sprayed both internally and externally, using a misting hand-held nozzle, with 200 mL of the 3% solution of Stabrom 909 biocide (SSBC). Previous quality control trials using dye had ensured that complete carcass coverage was achieved with the use of 200 mL of liquid spray. The spray was allowed to stay on the warm carcasses for 60 seconds.
b) The treatment on sampling day 0 of 102 total of the remaining 110 carcasses from each treatment involving "whole bird" washing and *Salmonella* detection, all as described in Example 6, was applied only to the birds of Test Groups 1–4 (note Table 38).

Figure 3:
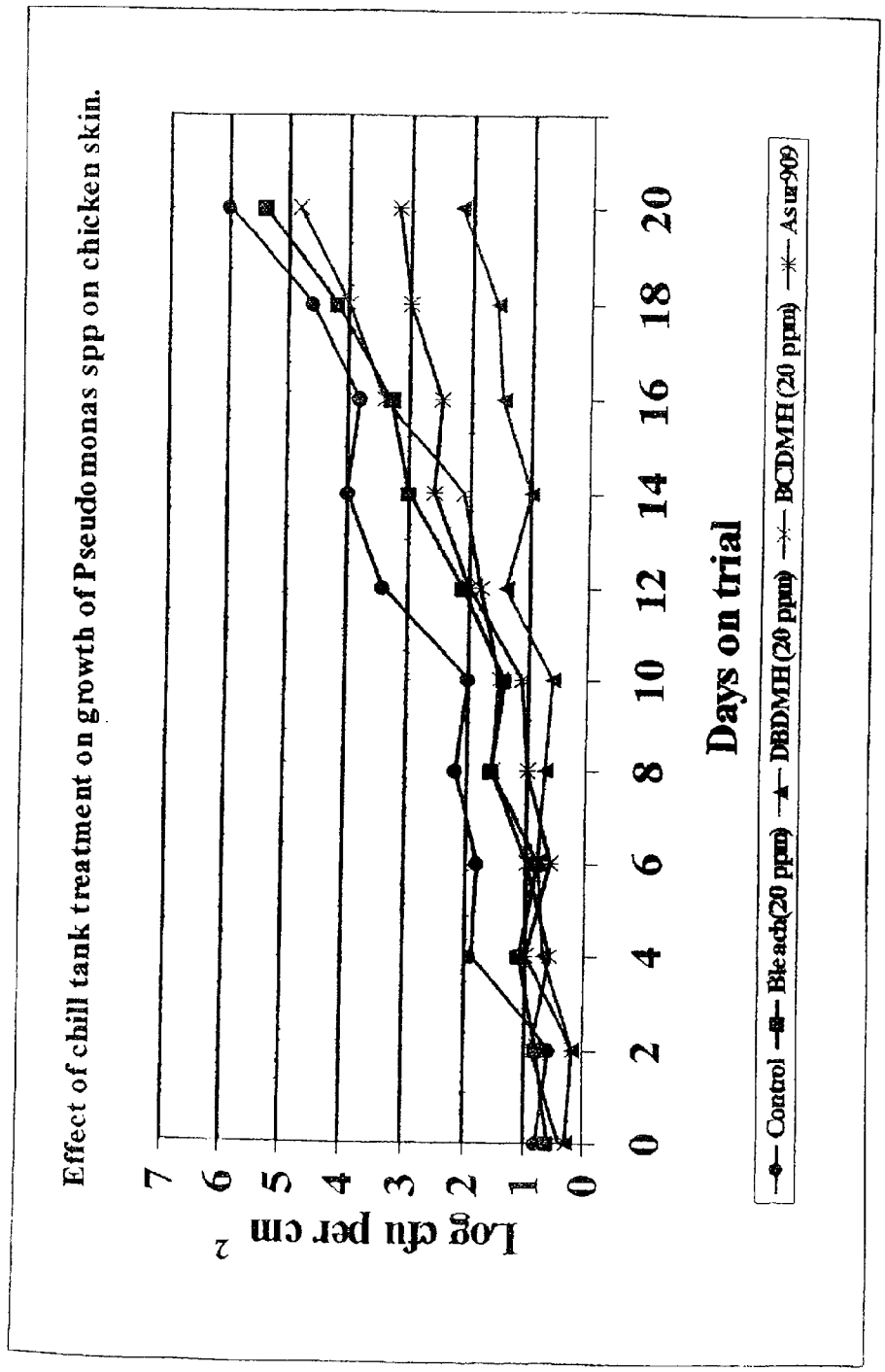
FIG. 3 is a graphical depiction of the effect of chill tank microbiocidal treatments on growth of Pseudomonas species on chicken skin.
Figure 4:
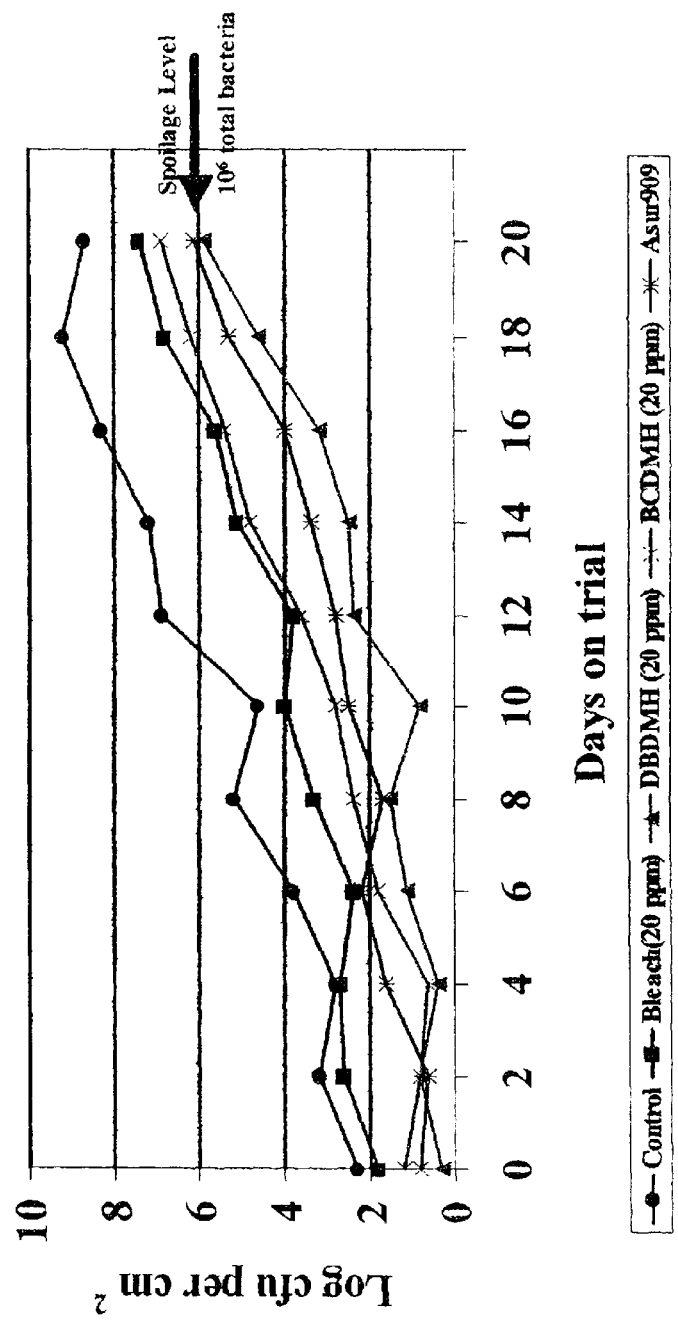
FIG. 4 is a graphical depiction of the effect of chill tank microbiocidal treatments on growth of total aerobic bacteria on chicken skin.

Tables 39–42 summarize the results of this group of tests. The effect of the chill tank treatment of this Example on growth of *Pseudomonas* species on chicken skin are graphically depicted in FIG. 3. FIG. 4 depicts graphically the results of the tests of this Example on the effect of chill tank treatment on growth of total aerobic bacteria on the chicken skin.

TABLE 39

| Water Treatment | Salmonella positive samples (Number 51)[1] (Birds were inoculated with Salmonella prior to chilling) |
|---|---|
| None (Control) | 21/51 (41.18%) |
| Clorox ® bleach (20 ppm) | 8/51 (15.68%) |
| DBDMH (20 ppm Cl$_2$ equivalent) during chilling | 1/51 (1.96%) |
| BCDMH (20 ppm Cl$_2$ equivalent) during chilling | 6/51 (11.76%) |

[1]Twelve (12) per 51 or less is considered to be statistically acceptable by USDA HACCP standards. A total of 102 birds were used to determine salmonella positive samples and a simple average determined.

TABLE 40

| Water Treatment | Bloating (Number per 60 birds processed)[1] |
|---|---|
| None (Control) | 0/120 (0.00%) |
| Clorox ® bleach (20 ppm) | 0/120 (0.00%) |
| DBDMH (20 ppm Cl$_2$ equivalent) during chilling | 0/120 (0.00%) |
| BCDMH (20 ppm Cl$_2$ equivalent) during chilling | 0/120 (0.00%) |

[1]Four (4) or more per treatment is considered to be highly objectionable.

TABLE 41

| | Sensory Score (days post-processing)[1,2] | | | |
|---|---|---|---|---|
| Water Treatment | 5 days | 10 days | 15 days | 20 days |
| None (Control) | 2.4 b | 4.8 c | 6.9 c | 9.0 d |
| Clorox ® bleach (20 ppm) | 1.3 ab | 2.4 b | 4.6 b | 6.8 c |
| DBDMH (20 ppm Cl$_2$ equivalent) during chilling | 0.6 a | 1.2 a | 3.2 a | 3.4 a |
| BCDMH (20 ppm Cl$_2$ equivalent) during chilling | 1.4 ab | 1.8 ab | 2.7 a | 4.8 b |

[1]Continuous scale for non-structured fresh inside carcass odor sensory attributes ranges from value 1.0 (the lowest intensity) to value 9.0 (the highest intensity). NOTE: Means within a row without a common superscript are significantly different (P < 0.05) as determined by Least Significant Difference.
[2]Five (5) or more is considered to be highly objectionable.

TABLE 42

| Water Treatment | Skin Pigmentation | | | | | |
|---|---|---|---|---|---|---|
| | Mean Pre-Chill Minolta Value[2] | | | Mean Post-Chill Minolta Value[2] | | |
| | L | a | b | L | a | b |
| None (Control) | 52.61 a | 3.25 a | 11.43 a | 47.21 a | 4.24 a | 12.44 a |
| Clorox ® bleach (20 ppm) | 52.76 a | 3.32 a | 11.84 a | 47.43 a | 4.85 a | 12.67 a |
| DBDMH (20 ppm $Cl_2$ equivalent) during chilling | 52.23 a | 3.13 a | 11.63 a | 48.02 a | 4.69 a | 12.47 a |
| BCDMH (20 ppm $Cl_2$ equivalent) during chilling | 52.11 a | 3.82 a | 11.26 a | 46.93 a | 4.44 a | 12.60 a |
| SSBC Carcass Spray (3% liquid pre-chill application) | 52.61 a | 3.67 a | 11.15 a | 47.03 a | 4.51 a | 12.55 a |

[1]NOTE: Means within a row without a common superscript are significantly different (P < 0.05) as determined by Least Significant Difference.
[2]Skin pigmentation (Minolta Color Meter L value or Lightness, a value or redness and b value or yellowness)
[3]All treatment skin pigmentation were measured on 120 birds, except for SSBC where only 10 birds were employed.

A number of tests have been carried out demonstrating the microbiocidal effectiveness of several microbiocides in eradicating or controlling various bacteria species of the types present in poultry processing systems.

One such series of tests involved determinations of microbiological control against *Escherichia coli* bacteria. Another set of tests involved determinations of microbiological control against *Enterococcus faecium*. In each case, comparative tests were carried out in the same manner utilizing the AOAC test method. Such test involves exposing a culture of the microorganism to various concentrations of a test solution prepared from an aqueous stock solution of the compound under test. At various time intervals the halogen in the test suspensions is chemically neutralized, and the amount of viable bacteria remaining is enumerated by plating onto nutrient agar and incubating for 2 days at 37° C. Results are expressed at the $\log_{10}$ colony forming units (CFU). The concentration of the compound required to achieve complete kill (i.e., no viable bacteria remain) within 30 seconds is determined in the test.

Table 43 summarizes the data obtained in the tests using respectively, 1,3-dibromo-5,5-dimethylbydantoin (DBDMH) and N,N'-bromochloro-5,5-dimethylhydantoin (BCDMH) and in which the microorganism in each case was *Escherichia coli*. It can be seen that 1,3-dibromo-5,5-dimethylhydantoin passed the test at one milligram of bromine, as $Br_2$, per liter of water, as evidenced by the complete kill within 30 seconds, whereas 1,3-bromochloro-5,5-dimethylhydantoin required two milligrams of bromine, as $Br_2$, per liter of water to achieve complete kill within 30 seconds.

TABLE 43

EFFECTIVENESS AGAINST *ESCHERICHIA COLI*

| Concentration mg/L as $Br_2$ | Contact Time | $\log_{10}$ CFU Recovered Using DBDMH | $\log_{10}$ CFU Recovered Using BCDMH |
|---|---|---|---|
| 0.5 mg/L | 30 sec | >4.48 | >4.48 |
| | 1 min | 1.70 | 4.46 |
| | 2 min | 0 | 1.65 |
| | 3 min | 0 | 0 |
| | 4 min | 0 | 0 |
| | 5 min | 0 | 0 |
| | 10 min | 0 | 0 |
| 1.0 mg/L | 30 sec | 0 | >4.48 |
| | 1 min | 0 | 0.7 |
| | 2 min | 0 | 0 |
| | 3 min | 0 | 0 |
| | 4 min | 0 | 0 |
| | 5 min | 0 | 0 |
| | 10 min | 0 | 0 |
| 2.0 mg/L | 30 sec | 0 | 0 |
| | 1 min | 0 | 0 |
| | 2 min | 0 | 0 |
| | 3 min | 0 | 0 |
| | 4 min | 0 | 0 |
| | 5 min | 0 | 0 |
| | 10 min | 0 | 0 |

Table 44 summarizes the data obtained in the tests using respectively 1,3-dibromo-5,5 methylhydantoin (DBDMH) and N,N'-bromochloro-5,5-dimethylhydantoin (BCDMH) and in which the microorganism in each case was *Enterococcus faecium*. Table 44 shows that 1,3-dibromo-5,5-dimethylhydantoin passed the test at one milligram of bromine, as $Br_2$, per liter of water, as evidenced by the complete kill within 30 seconds, whereas N,N'-bromochloro-5,5-dimethylhydantoin required two milligrams of bromine, as $Br_2$, per liter of water to achieve complete kill within 30 seconds.

TABLE 44

EFFECTIVENESS AGAINST *ENTEROCOCCUS FAECIUM*

| Concentration mg/L as $Br_2$ | Contact Time | $\log_{10}$ CFU Recovered Using DBDMH | $\log_{10}$ CFU Recovered Using BCDMH |
|---|---|---|---|
| 0.5 mg/L | 30 sec | 4.32 | >4.48 |
| | 1 min | 2.36 | 3.53 |
| | 2 min | 0.00 | 2.63 |
| | 3 min | 0.00 | 0.00 |
| | 4 min | 0.00 | 0.00 |
| | 5 min | 0.00 | 0.00 |
| | 10 min | 0.00 | 0.00 |
| 1.0 mg/L | 30 sec | 0.00 | >4.48 |
| | 1 min | 0.00 | 2.38 |
| | 2 min | 0.00 | 0.00 |
| | 3 min | 0.00 | 0.00 |
| | 4 min | 0.00 | 0.00 |
| | 5 min | 0.00 | 0.00 |
| | 10 min | 0.00 | 0.00 |
| 2.0 mg/L | 30 sec | 0.00 | 0.00 |
| | 1 min | 0.00 | 0.00 |
| | 2 min | 0.00 | 0.00 |
| | 3 min | 0.00 | 0.00 |
| | 4 min | 0.00 | 0.00 |
| | 5 min | 0.00 | 0.00 |
| | 10 min | 0.00 | 0.00 |

Table 45 summarizes test results performed at MBEC Bioflim Technologies, Inc., Calgary, Canada on the effectiveness of various biocides on bioflim removal. The test procedure, developed at the University of Calgary, utilizes a device which allows the growth of 96 identical biofilms under carefully controlled conditions. The device consists of a two-part part vessel comprised of an upper plate containing 96 pegs that seals against a bottom plate. The bottom plate can consist of either a trough (for biofilm growth) or a standard 96-well plate (for biocide challenge). The biofilms develop on the 96 pegs. The device has been used as a general method for evaluating the efficacy of antibiotics and biocides towards biofilms. See in this connection H. Ceri, et al., "The MREC Test: A New In Vitro Assay Allowing Rapid Screening for Antibiotic Sensitivity of Biofilm", Proceedings of the ASM, 1998, 89, 525; Ceri, et al., "Antifungal and Biocide Susceptibility testing of Candida Biofilms using the MBEC Device", Proceedings of the Interscience Conference on Antimicrobial Agents and Chemotherapy, 1998, 38, 495; and H. Ceri, et al., "The Calgary Biofilm Device: A New Technology for the Rapid Determination of Antibiotic Susceptibility of Bacterial Biofilms", Journal of Clinical Microbiology, 1999, 37, 1771–1776.

Six biocide systems were evaluated using the above test procedure and test equipment. Five of these systems were oxidizing biocides, viz., chlorine (from NaOCl), halogen (from NaOCl+NaBr), halogen (from BCDMH), bromine (from DBDMH), and chlorine (from trichloroisocyanuric acid), all expressed as bromine as $Br_2$ in mg/L, so that all test results were placed on the same basis. The sixth biocide was glutaraldehyde, a non-oxidizing biocide.

These biocide systems were used to challenge biofilms of Pseudomonas aeruginosa (ATCC 15442). This is a Gram (−) bacterium which is ubiquitous in microbiological slimes found in many water systems. See in this connection J. W. Costerton and H. Anwar, "Pseudomonas aeruginosa: The Microbe and Pathogen", in Pseudomonas aeruginosa Infections and Treatment, A. L. Baltch and R. P. Smith editors, Marcel Dekker publishers, New York, 1994. In the field of poultry processing, S. Notermans, J. Dormans, and G. C. Mead, Biofouling, 1991, Vol. 5, pages 21–36, report observation of biofilms in poultry slaughter houses by use of scanning electron microscopy.

In Table 45 the MBEC (minimum biofilm eradication concentration) results presented are for the one-hour biocide contact time used in the test. The values given for the halogen containing biocides are expressed in terms of mg/L of bromine as $Br_2$. The data on the glutaraldehyde is in terms of mg/L as active ingredient. The data indicate that the DBDMH was more effective than any of the other biocides tested under these conditions with an MBEC of 1.4 mg/L of bromine, as $Br_2$. In fact, only slightly more than one-half as much bromine from DBDMH was required to remove the biofilm as compared to the total halogen, expressed as $Br_2$, that was required from BCDMH.

TABLE 45

EFFECTIVENESS AGAINST PSEUDOMONAS AERUGINOSA BIOFILM

| Biocide System | MBEC | MBEC, avg. |
| --- | --- | --- |
| Chlorine (from NaOCl) | 5.0, 2.5 | 3.8 |
| Halogen (from NaOCl + NaBr) | 2.5, 2.5 | 2.5 |
| Halogen (from BCDMH) | 2.5, 2.5 | 2.5 |
| Bromine (from DBDMH) | 1.4, 1.4 | 1.4 |
| Chlorine (from Trichloroisocyanuric acid) | 2.6, 1.3 | 2.0 |
| Glutaraldehyde | 50, 50 | 50 |

In another group of tests, the results of which are depicted in FIGS. 5 through 10, several bromine-based microbiocides of this invention were utilized in tests illustrating their effectiveness in eradicating or controlling Heterotrophic Plate Count bacteria i.e., a mixture of naturally-occurring pathogenic bacteria of various unidentified species. These bacteria were challenged both in the form of biofilms and in planktonic form.

The experimental conditions utilized in these tests involved use of an apparatus consisting of three parallel transparent PVC sampling pipes. These pipes were used for collection of biofilm (i.e., sessile or surface attached) bacteria samples; one as control pipe, one for a relatively low biocide concentration and the third for a higher biocide concentration. The biocide challenge in each case was divided into three phases. First was a 14-day inoculation. Next was a 48-hour disinfection period. Finally a 2-week recovery period was provided. The biocide under test was slug-dosed and during the fist hour of exposure, the concentration was adjusted to achieve the desired concentration level.

The source of the naturally-grown heterotrophic plate count (HPC) bacteria was sediment and associated water collected from the recirculating hot water system of a hospital. Filter cartridges were inserted into the hospital water system and after about two months a suitable amount of sediment had accumulated on the filters. The collected filter/water suspension was then harvested for culturing. The inoculum for the biocide challenge experiments consisted of dechlorinated tap water, HPC-cultured stock solution, and a nutrient supplement solution. The inoculum was incubated at 37° C. for 14-days prior to the start of the test. The inoculum along with additional dechlorinated tap water was introduced into the apparatus composed of the three parallel transparent PVC sampling pipes. This mixture was recirculated throughout the apparatus intermittently at the rate of 3.2 gallons per minute for 14-days to produce a consistent biofilm and planktonic HPC bacteria population.

Samples of these bacteria were collected at the end of the 14-day inoculation period before the biocide challenge. In each test, the HPC bacteria was then challenged with a specified level of abromine-based biocide, and samples were taken at 1, 2, 3, 12, and 48-hour intervals. These samples were taken by swabbing the inner surface of a prepeasured section (length, $17/32$ inch) of the transparent PVC sampling pipe. The swabs were vortexed for 1 minute in 5 mL of deionized water with 0.1 mL of a neutralizer (to remove residual bromine) before plating. Con currently, water samples were taken for enumeration of the planktonic HPC bacteria.

After the 48-hour biocide challenge period, the procedure involved providing the 2-week recovery period. The purpose of providing this recovery period was to determine how quickly the viable HPC bacteria that were still present repopulated both the biofilm and, in planktonic form, the recirculating water. Thus, the recirculating water was drained from the test apparatus and the apparatus was refilled with heat-sterilized tap water which was also allowed to recirculate intermittently as before. After 7 and 14 days the apparatus was resampled and biofilm and planktonic HPC bacteria were enumerated in the same manner as done previously.

The results of these test are presented in graphical for in the FIGS. 5 through 10. In the tests of FIG. 5 the active bromine species derived from sulfamate-stabilized bromine chloride (Stabrom® 909 biocide, Albemarle Corporation) were employed respectively at 0.5 ppm and at 2 ppm, both as bromine, to challenge biofilm-associated HPC bacteria. In addition a control was carried out in the same manner except that no biocide was applied. It can be seen that at the higher bromine concentration, within three hours almost 99% of the biofilm-associated HPC bacteria were eradicated, whereas at 0.5 ppm as bromine, around 95% of the HPC bacteria were eradicated. It can also be seen that at both levels of active bromine concentration, very little recovery of the biofilm HPC bacteria occurred during the 48-hour biocide challenges period. Furthermore, even after the full two-week recovery period, the HPC biofilm bacteria had still not reestablished their original population level.

In FIG. 6 the active bromine species used in the tests and their concentrations were the same as in FIG. 5, and a control was used. However, in these tests the HPC bacteria were in planktonic form. It can be seen that at the higher bromine concentration, within three hours over 90% of the planktonic HPC bacteria were eradicated, and at 0.5 ppm as bromine, approximately 85% of the planktonic HPC bacteria were eradicated. These test results also indicate that even at these low levels of active bromine, the planktonic HPC bacteria were not able to reestablish populations equal to their original levels during the 2-week recovery period.

The results depicted in FIG. 7 involved use of higher concentrations of the active bromine species derived from sulfamate-stabilized bromine chloride (Stabrom® 909 biocide) than the tests of FIG. 5. In particular, this microbiocide was employed respectively at 4 ppm and at 10 ppm, both as bromine, to challenge biofilm-associated HPC bacteria. In addition, a control was carried out in the same manner except that no biocide was applied. It can be seen that at the higher bromine concentration, within three hours almost 99.9% of the biofilm-associated HPC bacteria were eradicated. At 4 ppm as bromine, almost 99% of the HPC bacteria were eradicated within three hours. It can also be seen that at both levels of active bromine concentration, very little recovery of the biofilm HPC bacteria occurred during the 48-hour biocide challenge period. Furthermore, even after the full two-week recovery period, the HPC biofilm bacteria had still not reestablished populations close to their original levels.

In FIG. 8 the active bromine species used and their concentrations were the same as in FIG. 7, and a control was used. However, in these tests the HPC bacteria were in planktonic form. It can be seen that at both bromine concentration, within three hours over 99% of the planktonic HPC bacteria were eradicated. It can also be seen that within the 48-hour biocide challenge period, recovery of the very small amounts of the viable planktonic HPC bacteria that still remained had hardly begun to occur in either of the tests in which the bromine biocide was used. These test results also indicate that for the planktonic HPC bacteria to reestablish populations close to their original levels, a recovery period of substantially more than two weeks would be required.

The test results depicted in FIG. 9 involved use of 1,3-dibromo-5,5-dimethylhydantoin (Albrome® 100 biocide, Albemarle Corporation) as the source of active bromine species. This microbiocide was used in these tests at levels of 0.5 ppm and 5 ppm as bromine to challenge biofilm-associated HPC bacteria. Also, a control was carried out in the same manner except that no biocide was applied. It can be seen from FIG. 9 that at the higher bromine concentration, within twelve hours almost 99.9% of the HPC bacteria were eradicated. At 0.5 ppm as bromine, over 99% of the HPC bacteria were eradicated within three hours. It can also be seen that within the 48-hour biocide challenge period, the very small amounts of the viable HPC biofilm that still remained were beginning to recover in both tests in which the bromine biocide was used. These test results also indicate that for the HPC bacteria to reestablish populations close to their original levels, a recovery period of substantially greater than two weeks would have been required.

In the tests of FIG. 10 the active bromine species used and their concentrations were the same as in FIG. 9, and a control was used. However, in these tests the HPC bacteria were in planktonic form. It can be seen that at the higher bromine concentration, almost 99.99% of the planktonic HPC bacteria were eradicated within twelve hours. At 0.5 ppm as bromine and within three hours, almost 99% of the planktonic HPC bacteria were eradicated. It can also be seen that within the 48-hour biocide challenge period, the very small amounts of the viable planktonic HPC bacteria that still remained were beginning to recover in both tests in which the bromine biocide was used. These test results also indicate that for the planktonic HPC bacteria to reestablish populations close to their original levels, a recovery period of more than two weeks would have been required.

In the practice of this invention, combinations of different sanitizing steps using different microbiocidal agents, at least one of which is a microbiocide of this invention, preferably one or more bromine-based microbiocidal agents of this invention, can prove useful. For example, a microbiocide of this invention, preferably a bromine-based microbiocide of this invention, can be applied to or contacted with various surfaces associated with the poultry processing such as conduits, tanks (e.g., the scalding tank(s), chill tank(s), conveyor belts or conveyor lines, and the poultry carcasses themselves can be treated with an antimicrobial agent such as solutions or gels containing carboxylic acids (e.g., acetic or lactic acid) and/or peroxycarboxylic acids, such as peracetic acid, peroxyoctanoic acid, peroxydecanoic acid, or the like. Use of such carboxylic acids is described for example in U.S. Pat. No. 6,113,963. The result of such combined operations is highly effective sanitization. In fact, it is contemplated that this combination of operations will result in a greater extent of microbiological eradication than has been generally achievable heretofore, especially when the bromine-based biocide used is 1,3-dibromo-5,5-dimethylhydantoin and the carboxylic acid used is peracetic acid. Indeed the combined effect of these microbiocides maybe synergistic.

Another microbiocide which can be utilized in combined operations pursuant to this invention is trisodium phosphate, a material which according to Capita et al., *Meat Science,* 2000, 55 (4), 471–474, has been approved by the USDA as an aid to eliminate *Salmonella* on raw poultry carcasses. In the combined operations trisodium phosphate is applied to the poultry carcasses, and one or more of the microbiocides of this invention, preferably one or more of the bromine-based microbiocides of this invention, are utilized in sanitizing the equipment, instruments, and/or apparatus associated with the processing of the poultry. Also pursuant to this invention the combined operations can utilize chlorine dioxide treatments along with use of the microbiocides of this invention. Smith, *Meat Processing,* 1996, 35(10), 47 indicates that chlorine dioxide had been approved by the US FDA for use in poultry processing water, and in the practice of this invention one or more microbiocides of this invention, preferably one or more of the bromine-based microbiocides of this invention, are utilized in sanitation of various items of equipment, instruments, and/or apparatus utilized in the processing of the poultry, and chlorine dioxide is used to sanitize at least some of the poultry processing water.

Another way by which combined operations pursuant to this invention can be carried out involves administering to the digestive tract of the poultry a suitable biological pathogen-control agent, such as by including such biological agent in the drinking water for the fowl, or on or in the feed for the fowl. Illustrative biological pathogen-control agents which may be used in this manner include certain strains of E. coli described in U.S. Pat. No. 6,083,500. Thus in the practice of this invention, such a biological pathogen-control agent is provided to the fowl for consumption by drinking and/or eating, and a microbiocidally-effective amount of an aqueous solution of at least one microbiocide of this invention, which preferably is at least one bromine-based microbiocide of this invention, is used in disinfecting or sanitizing equipment, instruments, apparatus, and/or water used in the processing of poultry, and/or of carcasses and/or parts of poultry resulting from the processing of poultry.

Still another combined operation involves (i) treating the carcasses of the fowl with immobilized lactoferrin antimicrobial agents as described in U.S. Pat. No. 6,172,040 B1 and (ii) disinfecting or sanitizing all or a portion of the equipment, instruments, apparatus, and/or water used in the processing of poultry by contacting the same with a microbiocidally-effective amount of an aqueous solution of at least one microbiocide of this invention, which preferably is at least one bromine-based microbiocide of this invention.

Automated dispensing equipment suitable for use in dispensing the microbiocides of this invention has been described in the literature and to at least some extent is available in the marketplace. For a reference to such equipment, see for example U.S. Pat. No. 5,683,724 wherein an automated dispensing system is described.

While chemists understand what is meant by "aqueous" in connection with a solution or medium or the like, it is probably desirable to state for the benefit of those lawyers who may make it a profession to pettifog over every word someone uses, just what "aqueous" means. The adjective "aqueous" means that the solution or medium or whatever other noun the adjective modifies, can be water whether highly purified or of ordinary purity such as emanates from the faucet. Since we are dealing with processing of food, it stands to reason that one would not use sewer water or water containing lethal doses of poisons such as cyanide. Besides naturally-occurring trace impurities that may be present in, say, potable water in general, such as ordinary well water or municipal water, the adjective "aqueous" also permits the presence in the water of dissolved salts that are formed in the course of forming a bromine-based microbiocide in the water, e.g., by reaction between bromine chloride and sodium sulfamate in an overbased aqueous solution. In addition, "aqueous" permits the presence of small amounts of innocuous non-harmful, water-soluble organic solvents such as ethyl alcohol which can be used as a solvent for the 1,3-dihalo-5,5-dialkylhydantoin(s). Also "aqueous" permits the presence in the water of the amount of the halogen-based microbiocide itself to the extent that it may dissolve in the water, plus any dissolved reactant(s) that may remain after the reaction. Also the water may contain a few atoms that may dissolve from the vessel in which the reaction takes place, plus air-borne impurities that may find their way into the water. The point here is that the term "aqueous" does not restrict the medium or solvent to absolutely pure water—the aqueous solution or medium or the like can contain what would normally be present and/or reasonably be expected to be present in it under the particular circumstances involved when employing ordinary common sense.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what chemical changes, if any, take place in the resulting mixture or solution, as such changes are the natural result of bringing the specified substances together under the conditions called for pursuant to this disclosure. As an example, the phase "solution of at least one 1,3-dihalo-5,5-dialkylhydantoin" and phrases of similar import signify that just before being brought into contact with an aqueous medium such as water, the at least one 1,3-dihalo-5,5-dialkylhydantoin referred to was the specified 1,3-dihalo-5,5-dialkylhydantoin. The phrase thus is a simple, clear way of referring to the solution, and it is not intended to suggest or imply that the chemical exists unchanged in the water. The transformations that take place are the natural result of bringing these substances together, and thus need no further elaboration.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as maybe expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

All documents referred to herein are incorporated herein by reference in toto as if fully set forth in this document.

This invention is susceptible to considerable variation within the spirit and scope of the appended claims.

That which is claimed is:

1. In a process of slaughtering poultry, which comprises a step wherein the poultry carcasses or parts thereof are washed with water, the improvement comprising introducing into said water in an amount effective to provide microbiocidal activity, a halogen-based microbiocide which as introduced is in the form of (i) at least one 1,3-dibromo-5,5-dialkylhydantoin in which one of the alkyl groups is a methyl group and the other alkyl group contains in the range of 1 to about 4 carbon atoms, or (ii) an aqueous microbiocidal solution of one or more active halogen species, which solution is a derivative product in an aqueous medium of at least one 1,3-dibromo-5,5-diallylhydantoin in which one of the alkyl groups is a methyl group and the other alkyl group contains in the range of 1 to about 4 carbon atoms, or (iii) both (i) and (ii).

2. The improvement of claim 1 wherein said microbiocide comprises (i) at least one 1,3-dibromo-5,5-dialkylhydantoin selected from the group consisting of 1,3-dibromo-5,5-dimethylhydantoin, 1,3-dibromo-5-ethyl-5-methylhydantoin, 1,3-dibromo-5-n-propyl-5-methylhydantoin, and 1,3-dibromo-5-isobutyl-5-methylhydantoin, or (ii) an aqueous microbiocidal solution of one or more active halogen species, which solution is a derivative product in an aqueous medium of at least one 1,3-dibromo-5,5-dialkylhydantoin selected from the group consisting of 1,3-dibromo-5,5-dimethylhydantoin, 1,3-dibromo-5-ethyl-5-methylhydantoin, 1,3-dibromo-5-n-propyl-5-methylhydantoin, and 1,3-dibromo-5-isobutyl-5-methylhydantoin, or (iii) both (i) and (ii).

3. The improvement of claim 1 wherein said microbiocide is (i) 1,3-dibromo-5,5-dimethylhydantoin or (ii) an aqueous microbiocidal solution of one or more active halogen species, which solution is a derivative product in an aqueous medium of 1,3-dibromo-5,5-dimethylhydantoin, or (iii) both (i) and (ii).

4. In a process of slaughtering poultry, which comprises a step wherein poultry carcasses or parts thereof are washed with water, the improvement comprising introducing into said water in an amount effective to provide microbiocidal activity 1,3-dibromo-5,5-dimethylhydantoin in the form of solids or as a microbiocidal solution or slurry of 1,3-dibromo-5,5-dimethylhydantoin.

5. The improvement of any of claims 2, or 3, or 4 wherein said carcasses or parts thereof to be washed have therein or thereon at least one of *Escherichia coli, Pseudomonas aeruginosa, Salmonella enteritidis, Shigella sonnei, Listeria monocytogenes*, and *Campylobacter jejuni*.

6. In a process of slaughtering poultry, which comprises a step wherein poultry carcasses or parts thereof are washed with water, the improvement comprising introducing into said water as a microbiocide at least one 1,3-dibromo-5,5-dialkylhydantoin and/or an aqueous solution or slurry formed therewith, in an amount effective to control at least one of *Escherichia coli, Pseudomonas aeruginosa, Salmonella enteritidis, Shigella sonnei, Listeria monocytogenes*, and *Campylobacter jejuni*, said at least one 1,3-dibromo-5,5-dialkylhydantoin characterized in that one of the alkyl groups is a methyl group and the other alkyl group contains in the range of 1 to about 4 carbon atoms.

7. The improvement of claim 6 wherein at least a portion of said 1,3-dibromo-5,5-dialkylhydantoin is introduced as 1,3-dibromo-5,5-dialkylhydantoin, and wherein one or more active bromine species are formed in situ in said water.

8. The improvement of claim 6 wherein said microbiocide includes at least 1,3-dibromo-5,5-dimethylhydantoin and/or an aqueous solution or slurry formed therewith.

9. In the processing of poultry, the improvement which comprises disinfecting carcasses and/or other parts of poultry resulting from such processing, with a halogen-based microbiocide which is an aqueous microbiocidal solution ofone or more active halogen species, which solution is a derivative product in an aqueous medium of at least one 1,3-dibromo-5,5-dialkylhydantoin in which one of the alkyl groups is a methyl group and the other alkyl group contains in the range of 1 to about 4 carbon atoms.

10. The improvement of claim 9 wherein the microbiocide used comprises a microbiocidal amount of an aqueous microbiocidal solution of one or more active halogen species, which solution is a derivative product in an aqueous medium of at least one 1,3-dibromo-5,5-dialkylhydantoin in which one of the alkyl groups is a methyl group and the other alkyl group contains in the range of 1 to about 4 carbon atoms.

11. The improvement of claim 9 wherein the microbiocide used comprises a microbiocidal amount of an aqueous microbiocidal solution of one or more active halogen species, which solution is a derivative product in an aqueous medium of 1,3-dibromo-5-isobutyl-5-methylhydantoin, 1,3-dibromo-5-n-propyl-5-methylhydantoin, or 1,3-dibromo-5-ethyl-5-methylhydantoin, or of any two or all three thereof.

12. The improvement of claim 9 wherein the microbiocide used comprises a microbiocidal amount of an aqueous microbiocidal solution ofone or more active halogen species, which solution is a derivative product in an aqueous medium of at least two of said 1,3-dibromo-5,5-dialkylhydantoins in which one of them is 1,3-dibromo-5,5-dimethylhydantoin.

13. The improvement of claim 9 wherein the microbiocide used comprises a microbiocidal amount of an aqueous microbiocidal solution of one or more active halogen species, which solution is a derivative product in an aqueous medium of 1,3-dibromo-5,5-dimethylhydantoin and of 1,3-dibromo-5-ethyl-5-methylhydantoin.

14. The improvement of claim 9 wherein the microbiocide used comprises a microbiocidal amount of an aqueous microbiocidal solution of one or more active halogen species, which solution is a derivative product in an aqueous medium of 1,3-dibromo-5,5-dimethylhydantoin.

15. The improvement of any of claims 9 to 14, both inclusive, wherein the carcasses and/or other parts of poultry resulting from such processing being disinfected has therein or thereon at least one of *Escherichia coli, Salmonella enteritidis, Salmonella typhimurim, Campylobacter jejuni, Campylobacter coli, Campylobacter lari, Listeria monocytogenes, Pseudomonas fluorescens, Pseudomonas aeruginosa, Enterococcus faecium*, and *Staphylococcus aureus*.

16. In the processing of poultry, the improvement which comprises disinfecting carcasses and/or other parts of poultry resulting from such processing, with a halogen-based microbiocide comprising an aqueous microbiocidal solution of at least one 1,3-dibromo-5,5-dialkylhydantoin in which one of the alkyl groups is a methyl group and the other alkyl group contains in the range of 1 to about 4 carbon atoms.

17. The improvement of claim 16 wherein the microbiocide used in forming said aqueous microbiocidal solution is at least one 1,3-dibromo-5,5-dialkylhydantoin in which one of the alkyl groups is a methyl group and the other alkyl group contains in the range of 1 to about 4 carbon atoms.

18. The improvement of claim 17 wherein said at least one 1,3-dibromo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, or any two or all three thereof.

19. The improvement of claim 17 wherein said at least one 1,3-dibromo-5,5-dialkylhydantoin is a mixture of at least two of said 1,3-dibromo-5,5-dialkylhydantoins in which one of them is 1,3-dibromo-5,5-dimethylhydantoin.

20. The improvement of claim 17 wherein said at least one 1,3-dibromo-5,5-dialkylhydantoin is a mixture of 1,3-dibromo-5,5-dimethylhydantoin and 1,3-dibromo-5-ethyl-S-methylhydantoin.

21. The improvement of claim 17 wherein said at least one 1,3-dibromo-5,5-dialkylhydantoin is 1,3-dibromo-5,5-dimethylhydantoin.

22. The improvement of any of claims 16 to 21, both inclusive, wherein parts of poultry being disinfected in such processing has therein or thereon at least one of *Escherichia coli, Salmonella enteritidis, Salmonella typhimurim, Campylobacter jejuni, Campylobacter coli, Campylobacter lari, Listeria monocytogenes, Pseudomonas fluorescens, Pseudomonas aeruginosa, Enterococcus faecium*, and *Staphylococcus aureus*.

* * * * *